(12) United States Patent
Polacheck et al.

(10) Patent No.: US 8,377,934 B2
(45) Date of Patent: Feb. 19, 2013

(54) USE OF STILBENE DERIVATIVES FOR TREATMENT AND PREVENTION OF AQUATIC MOLD INFECTIONS

(75) Inventors: Itzhack Polacheck, Jerusalem (IL); Simon Tinman, Bat Hefer (IL); Rama Falk, Merchaviah (IL)

(73) Assignees: State of Israel, Ministry of Agriculture & Rural Development, Agricultural Research Organization, Bet Dagan (IL); Hadasit Medical Research Services and Development Ltd., Jerusalem (IL)

( * ) Notice: Subject to any disclaimer, the term of this patent is extended or adjusted under 35 U.S.C. 154(b) by 553 days.

(21) Appl. No.: 12/306,446

(22) PCT Filed: Jun. 27, 2007

(86) PCT No.: PCT/IL2007/000784
§ 371 (c)(1),
(2), (4) Date: May 18, 2009

(87) PCT Pub. No.: WO2008/001368
PCT Pub. Date: Jan. 3, 2008

(65) Prior Publication Data
US 2009/0252768 A1    Oct. 8, 2009

Related U.S. Application Data

(60) Provisional application No. 60/816,619, filed on Jun. 27, 2006.

(51) Int. Cl.
*A61K 31/53* (2006.01)
*A01N 25/00* (2006.01)

(52) U.S. Cl. ........................................ 514/245; 424/405

(58) Field of Classification Search ............... 514/245; 424/405
See application file for complete search history.

(56) References Cited

U.S. PATENT DOCUMENTS

| | | |
|---|---|---|
| 4,723,034 A | 2/1988 | Schirmer |
| 5,124,149 A | 6/1992 | Shapiro |
| 5,188,832 A | 2/1993 | Mehlhorn |
| 5,313,911 A | 5/1994 | Thomassen |
| 5,359,131 A | 10/1994 | Cardin |
| 5,464,837 A | 11/1995 | Mehlhorn |
| 5,504,081 A | 4/1996 | Loehr |
| 5,593,678 A | 1/1997 | Evans |
| 5,852,015 A | 12/1998 | Gluzman |
| 5,879,674 A | 3/1999 | Black |
| 5,997,846 A | 12/1999 | Burns |
| 6,054,454 A | 4/2000 | Schmid |
| 6,117,457 A | 9/2000 | Devos |
| 6,160,023 A | 12/2000 | Braidwood |

(Continued)

FOREIGN PATENT DOCUMENTS

WO    WO/99/067418    12/1999

OTHER PUBLICATIONS

Willoughby et al. "Toward strategic use of fungicides against *Saprolegnia* parasitica in salmonid fish hatcheries," Journal of Fish Diseases, 1992, vol. 5, pp. 1-13.*

(Continued)

*Primary Examiner* — Shengjun Wang
(74) *Attorney, Agent, or Firm* — Rodney J. Fuller; Booth Udall Fuller, PLC

(57) ABSTRACT

The invention relates to methods of treatment and prevention of aquatic mold infections in aquatic organisms and methods of disinfecting equipment used in raising aquatic organisms. The methods comprise use of one or more stilbene derivatives, including 4,4'-bis-(1,3,5-triazinylamino)stilbene-2,2'-disulfonic acid derivatives.

28 Claims, 6 Drawing Sheets

U.S. PATENT DOCUMENTS

| | | |
|---|---|---|
| 6,365,737 B1 | 4/2002 | Metzger |
| 6,852,498 B2 | 2/2005 | Katagiri ........................ 435/7.8 |
| 6,875,421 B2 | 4/2005 | Burns |
| 6,919,452 B1 | 7/2005 | Kimura |
| 6,982,285 B2 | 1/2006 | Schmid |
| 2005/0230662 A1 | 10/2005 | Kimura |

OTHER PUBLICATIONS

The Center for Research Information, Inc "Calcofluor," Contract No. IOM-2794-04-01, The National Academies, 2004.*

International Search Report for PCT/IL2007/000784 dated Jun. 4, 2008 (2 sheets).

Written Opinion of the International Searching Authority for PCT/IL2007/000784 dated Jun. 4, 2008 (3 sheets).

Belliveau, Daniel J. et al., "Effects of fluorescent brighteners on growth and morphology of the red alga *Antithamnion kylinii*", Stain Technol, 65(6):303-311 (1990).

Inamori, Yoshihiko et al., "The biological activities of 3,4-O-isopropylidene-3,3'4,5'-tetrahydroxystilbene", Chem Pharm Bull (Tokyo), 33(7):2904-2909 (1985).

Roncero, Cesar et al , "Isolation and characterization of Saccharomyces cerevisiae mutants resistant to Calcofluor white", J Bacteriol, 170(4):1950-1954 (1988).

Roncero, Cesar and Duran, Angel, "Effect of Calcofluor white and Congo red on fungal cell wall morphogenesis: in vivo activation of chitin polymerization", J Bacteriol, 163(3):1180-1185 (1985).

Seppanen, S. -K. et al., "Antifungal activity of stilbenes in in vitro bioassays and in transgenic Populus expressing a gene encoding pinosylvin synthase", Plant Cell Rep, 22(8):584-593 (2004).

Blankophor safety sheet. Bayer. Date of Issue Feb. 6, 2003.

Stilbene Fluorescent Whitening Agents Category, submitted to the US Environmental Protection Agency by the ETAD Fluorescent Whitening Agent Task Force, Oct. 6, 2005.

* cited by examiner

USE OF STILBENE DERIVATIVES FOR TREATMENT AND PREVENTION OF AQUATIC MOLD INFECTIONS

RELATED APPLICATION DATA

This application is the U.S. national stage of PCT/IL2007/000784 filed on Jun. 27, 2007, which is based on and claims the benefit of U.S. Provisional Application No. 60/816,619 filed on Jun. 27, 2006, the content of each of which is expressly incorporated herein in its entirety by reference hereto.

FIELD OF THE INVENTION

The invention relates to compositions of stilbene derivatives useful in methods of treatment and prevention of mold infections in aquatic organisms such as fish and fish eggs.

BACKGROUND OF THE INVENTION

Oomycetes (water molds) such as *Saprolegnia, Branchiomyces* and *Aphanomyces* are responsible for devastating infections of fish in aquaculture, fish farms and hobby fish tanks.

Members of the genus *Saprolegnia* cause saprolegniosis, a disease that is characterized by visible white or grey patches of filamentous mycelium on the body or fins of freshwater fish. If untreated, infection with *Saprolegnia* species (spp.) leads to death by haemodilution. *Saprolegnia* spp. also infect fish eggs by adhesion to and penetration of the egg membrane. *Saprolegnia* spp. are considered opportunistic pathogens that are saprophytes. Infection frequently occurs during the winter, often resulting in large-scale "winter kill" epidemics. Conditions which promote proliferation of *Saprolegnia* spp. and their infectious zoospores include abrupt decreases in water temperatures and high density fish farming activities, and also appear to render fish vulnerable to infection due to increased physiological stress and immune system suppression.

*Saprolegnia parasitica* is one of the most economically damaging fish pathogens, causing losses of millions of dollars annually worldwide, particularly in the salmon and trout markets. In addition to being an opportunistic pathogen, some *S. parasitica* strains are highly virulent and cause primary infections.

Branchiomycosis is another infection occurring in fresh water fish, primarily in carp and eel. It is caused by *Branchiomyces sanguinis* and *B. demigrans*, with affected fish showing prominent gill necrosis and respiratory distress. The disease occurs most commonly in ponds with abundant organic matter, and high ammonia levels.

Parasitic infections are often concurrent with or accompany oomycete infections in commercial fish farming settings. Such parasitic infections include those caused by *Ichthyophthirius multifilis, Trichodina* spp., *Dactylogyrus* spp. and *Gyrodactylus* spp.

Oomycetes, including *Saprolegnia* spp. and *Branchiomyces* spp. are filamentous eukaryotic microorganisms which have many fungus-like characteristics, but are not true fungi. Like the true fungi, they feed on decaying matter and grow as branching filaments with non-septate hyphae. However, their cell wall is not composed of chitin (as in the true fungi) but is composed of a mixture of cellulosic compounds and other β-glucans. Further, oomycetes have several clearly defined developmental stages that are not found in fungi. Recent molecular studies have shown however, that closely related virulence components are shared between oomycetes and fungi.

Prior art methods for treatment of pathogenic oomycete infections, including saprolegniosis and branchiomycosis suffer from various disadvantages. The chemicals Diquat (a herbicide), benzalkonium chlorides, copper sulfate and potassium permanganate have all been disclosed to be useful for treatment of branchiomycosis. None of these however, are approved by the U.S. Food and Drug Administration for disease control in food fishes.

U.S. Pat. No. 6,160,023 discloses use of bronopol (2-bromo-nitropropane-1,3-diol) for treatment and prophylaxis of *S. parasitica* infections in fish, and for disinfecting equipment used in raising fish. This compound is mainly effective against infection present in fish eggs, but not that occurring in fish. In addition, it is relatively toxic to commercially important fish species.

Malachite green (4-[(4-dimethylaminophenyl)-phenylmethyl]-N,N-dimethyl-aniline) was previously widely used to control saprolegniosis. While this organic dye is very efficient at killing *S. parasitica*, its use has been banned since 2002 around the world, due to its carcinogenic, teratogenic and toxicological properties. This has resulted in a dramatic increase of *Saprolegnia* infections in commercial settings. Therefore, there is an urgent need for novel alternative methods of management of saprolegniosis.

Methods are also known for controlling parasitic infections in fish. U.S. Pat. No. 5,464,837 and U.S. Pat. No. 5,188,832 disclose use of triazine dione compounds; U.S. Pat. No. 5,313,911 discloses use of hydrogen peroxide; U.S. Pat. No. 6,054,454 discloses use of oxadiazine derivatives; U.S. Pat. No. 6,982,285 discloses use of benzoylurea derivatives; U.S. Pat. No. 6,117,457 discloses use of peracetic acid; U.S. Pat. No. 5,593,678 discloses use of orthovanadate salts; U.S. Pat. No. 5,504,081 discloses use of nitromethylene derivatives. None of these methods are known to be useful for simultaneous control of oomycete and parasitic infections.

Stilbene derivatives, including 4,4'-bis-(1,3,5-triazinylamino)stilbene-2,2'-disulfonic acid derivatives, are known fluorescent brightening agents which bind to polysaccharides having β-glucosidic linkages, including cellulose and chitin. Such compounds show antifungal activity, presumably due to interaction with and disruption of chitin microfibrils which constitute a major structural element in the fungal cell wall (Roncero et al. (1985) J. Bacteriol. 163:1180-1185). Antifungal effects of fluorescent brighteners have been demonstrated in true fungi which contain chitin in their cell walls, including plant pathogenic fungi (Seppanen et al. (2004) Plant Cell. Rep. 22:584-593), human pathogenic fungi-like yeasts (Roncero et al. (1988) J. Bacteriol. 170:1950-54), dermatophytes (Inamori et al. (1985) Chem. Pharm. Bull. (Tokyo) 33:2904-9) and red alga (Belliveau et al. (1990) Stain Technol. 65:303-311), but not in aquatic molds which contain cellulose instead of chitin in their cell walls.

U.S. Pat. No. 4,723,034 discloses 2-vinyl stilbene derivatives useful as fungicides for plant protection and wood preservation.

U.S. Pat. No. 5,359,131 and U.S. Pat. No. 5,852,015 disclose stilbene derivatives having anti-viral effects.

U.S. Pat. No. 5,879,674 discloses methods of protecting plant crops from insect attack by using stilbene derivatives to induce epizootic viral infections.

U.S. Pat. No. 6,919,452 and US patent application publication No. US 2005/0230662 disclose 4,4'-bis(1,3,5-triazinylamino)stilbene-2,2'-disulfonic acid derivatives and their use as fluorescent brightening agents.

Nowhere in the prior art is it taught or suggested that stilbene derivatives may be used to treat aquatic mold infections.

SUMMARY OF THE INVENTION

The present invention provides methods that are effective in prevention and treatment of oomycete infections in aquatic organisms. Advantageously, the methods of the invention involve use of compositions comprising known compounds which have negligible toxic effects and are acceptable for use even in aquatic species intended for human consumption. In particular, the present invention provides novel methods using stilbene derivatives for treatment and prevention of oomycete infections. The invention is based, in part, on the unexpected discovery that stilbene derivatives, including 4,4'-bis-(1,3,5-triazinylamino)stilbene-2,2'-disulfonic acid derivatives, are effective for prevention and treatment of oomycete infections, such as saprolegniosis, which occur in aquatic organisms including fish and fish eggs. The method of the invention is effective for application at both an early stage of infection, when no clinical signs may be apparent, as well as at later stages of infection when infection is established. Without wishing to be bound by any particular theory or mechanism of action, this activity may be due to the ability of such compounds to interfere with cell wall synthesis in oomycetes.

According to a first aspect, the present invention provides a method of preventing or treating a oomycete infection in an aquatic organism, the method comprising the step of contacting the aquatic organism with an effective amount of at least one 4,4'-bis-(1,3,5-triazinylamino)stilbene-2,2'-disulfonic acid derivative of Formula (I):

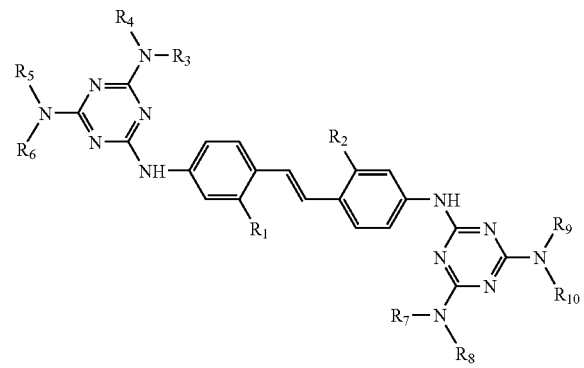

Formula (I)

wherein $R_1$ and $R_2$ are the same or different and are each independently selected from the group consisting of $SO_3H$, $SO_3Na$, $SO_3K$, $SO_3NH_4$ and H; and wherein $R_3$ to $R_{10}$ are the same or different and are selected from the group consisting of H; linear or branched $C_1$-$C_6$ alkyl; linear or branched $C_2$-$C_6$ alkenyl, wherein said alkyl or alkenyl are each independently unsubstituted or substituted with a hydroxyl, carboxyl, or carboxamide group; phenyl; and phenyl substituted with $R_1$ or $R_2$ wherein $R_1$ and $R_2$ are as defined above; or one or more of $R_3$ and $R_4$, $R_5$ and $R_6$, $R_7$ and $R_9$ or $R_5$ and $R_{10}$, together with the nitrogen to which they are attached, form a heterocyclic ring which can further comprise one or more additional heteroatoms selected from N, O and S; and salts, hydrates, solvates and polymorphs thereof.

According to another aspect, the present invention provides a method of disinfecting equipment used for raising an aquatic organism, wherein the equipment is contaminated with an oomycete, the method comprising the step of contacting the equipment with an effective amount of at least one 4,4'-bis-(1,3,5-triazinylamino)stilbene-2,2'-disulfonic acid derivative of Formula (I).

In particular embodiments of the methods of the invention, two or more of $R_3$, $R_4$, $R_7$ and $R_8$ are the same and are selected from the group consisting of $CH_2CH_2OH$, $CH_2CHOHCH_3$, $CH_2CH_2CONH_2$, $CH_3$ and H; or one or more of $R_3$ and $R_4$, $R_7$ and $R_8$ together with the nitrogen to which they are attached, form a morpholinyl ring. In other embodiments, two or more of $R_5$, $R_6$, $R_9$ and $R_{10}$ are the same and are selected from the group consisting of phenyl and phenyl substituted with $SO_3Na$. In other embodiments, $R_1$ and $R_2$ are the same and are selected from $SO_3H$ and $SO_3Na$. In still other embodiments, $R_1$ and $R_2$ are different and are selected from $SO_3H$, $SO_3Na$, $SO_3K$, $SO_3NH_4$ and H.

In specific embodiments of the methods of the invention, the 4,4'-bis-(1,3,5-triazinylamino)stilbene-2,2'-disulfonic acid derivative is selected from 4,4'-bis-(6-anilino-1,4-bis)-2-hydroxyethyl)amino)-1,3,5-triazin-2-yl)amino)stilbene-2, 2'-disulfonic acid;

disodium 4,4'-bis-(6-anilino-1,4-bis)-2-hydroxyethyl) amino)-1,3,5-triazin-2-yl)amino)stilbene-2,2'-disulfonate;

potassium sodium 4,4'-bis-(6-anilino-4-bis)-2-hydroxyethyl) amino)-1,3,5-triazin-2-yl)amino)stilbene-2,2'-disulfonate;

2,2'-stilbenedisulfonic acid,4,4'-bis-(4-anilino-6-((2-hydroxyethyl)methylamino)-s-triazin-2-yl)amino)-, disodium salt;

disodium 4,4'-bis[(4-anilino-6-morpholino-1,3,5-triazin-2-yl)amino]stilbene-2,2'-disulfonate;

tetrasodium 4,4'-bis[[4-[bis(2-hydroxyethyl)amino]-6-(4-sulfonatoanilino)-1,3,5-triazin-2-yl]amino]stilbene-2,2'-disulfonate;

tetrasodium 4,4'-bis[[4-[bis(2-hydroxypropyl)amino]-6-[(4-sulfonatophenyl)amino]-1,3,5-triazin-2-yl]amino]-stilbene-2,2'-disulfonate;

and 2,2'-stilbenedisulfonic acid,4,4'-bis-[[4-[(2-carbamoylethyl)(2-hydroxylethyl)amino]-6-(p-sulfoanilino)-s-triazin-2-yl]amino]-, tetrasodium salt.

In specific embodiments of the methods of the invention, the oomycete is selected from *Saprolegnia* spp., *Aphanomyces* spp. and *Branchiomyces* spp. In a more specific embodiment, the oomycete is *Saprolegnia parasitica*.

In specific embodiments of the methods of the invention, the at least one 4,4'-bis(1,3,5-triazinylamino)stilbene-2,2'-disulfonic acid derivative is provided as a solution. In other specific embodiments, the at least one 4,4'-bis-(1,3,5-triazinylamino)stilbene-2,2'-disulfonic acid derivative is present in the solution at a concentration of about 20 to about 200 mg/L. According to preferred embodiments, the at least one 4,4'-bis-(1,3,5-triazinylamino)stilbene-2,2'-disulfonic acid derivative is present in the solution at a concentration of about 25 mg/L.

In specific embodiments of the methods of the invention, the aquatic organism is selected from fish, fish eggs and shellfish. In specific embodiments, the fish are selected from barramundi, bass, bream, carp, catfish, chub, eel, elver, flounder, gilthead, guppy, halibut, koi, labrax, mullet, paddlefish, plaice, pompano, redfish, red-drum, salmon, sole, sturgeon, tilapia, trout, tuna and whitefish.

In specific embodiments of the methods of the invention, the contacting step is for a period of about 2 to about 16 hours.

In preferred embodiments, the contacting step is for a period of about 8 hours. In other embodiments, the contacting step is repeated at 48 hour intervals.

In one embodiment of the method of preventing or treating an oomycete infection in an aquatic organism, the oomycete infection is concurrent with or accompanied by a parasitic infection. In another embodiment, the parasitic infection is caused by at least one parasite selected from the group consisting of *Amyloodinium* spp., *Argulus* spp., *Ascocotyle* spp., *Bothricephalus* spp., *Camallanus* spp., *Capilaria* spp., *Centrocestus* spp., *Chilodonella* spp., *Coccidia* spp., *Contracaecum* spp., *Cryptobia* spp., *Cryptocaryon* spp., *Dactylogyrus* spp., *Dermocystidium* spp., *Ergasilus* spp., *Euclinostomum* spp., *Gyrodactylus* spp., *Hexamita* spp., *Ichtyobodo* spp., *Ichtyophtirius* spp., *Lernaea* spp., *Metacercarius* spp., *Microsporidia* spp., *Myxosporea* spp., *Oodinium* spp., *Sanguinicola* spp., *Sessiline* spp., *Spironucleus* spp., *Tetrahymena* spp., *Trichodina* spp., *Trichodinella* spp. and *Tripartiella* spp.

In one embodiment of the method of disinfecting equipment used for raising an aquatic organism, the equipment is further contaminated with at least one parasite. In another embodiment, the at least one parasite is selected from the group consisting of *Amyloodinium* spp., *Argulus* spp., *Ascocotyle* spp., *Bothricephalus* spp., *Camallanus* spp., *Capilaria* spp., *Centrocestus* spp., *Chilodonella* spp., *Coccidia* spp., *Contracaecum* spp., *Cryptobia* spp., *Cryptocaryon* spp., *Dactylogyrus* spp., *Dermocystidium* spp., *Ergasilus* spp., *Euclinostomum* spp., *Gyrodactylus* spp., *Hexamita* spp., *Ichtyobodo* spp., *Ichtyophtirius* spp., *Lernaea* spp., *Metacercarius* spp., *Microsporidia* spp., *Myxosporea* spp., *Oodinium* spp., *Sanguinicola* spp., *Sessiline* spp., *Spironucleus* spp., *Tetrahymena* spp., *Trichodina* spp., *Trichodinella* spp. and *Tripartiella* spp.

It is to be understood explicitly that the scope of the present invention encompasses variants of 4,4'-bis-(1,3,5-triazinylamino)stilbene-2,2'-disulfonic acid derivatives, such as salts, hydrates, solvates and polymorphs thereof, as are known in the art, with the stipulation that these variants must preserve the capacity to prevent and treat oomycete infections in aquatic organisms in the context of the present invention.

Other objects, features and advantages of the present invention will become clear from the following description and drawings. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
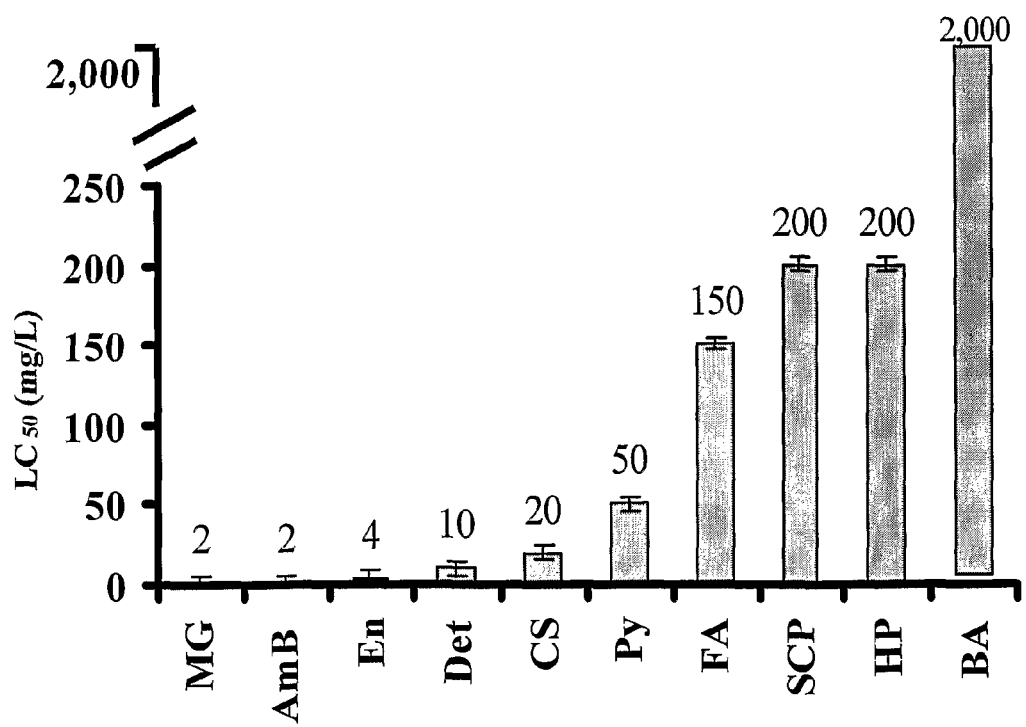
FIG. 1 illustrates the toxicity of various compounds in tilapia fish. MG, Malachite Green; AmB, Amphotericin B formulations; En, enilconazole; Det, detergents and disinfectants; CS, copper sulfate; Py, Pyceze®; FA, formaldehyde; SPC, sodium percarbonate; HP, hydrogen peroxide; BA, Blankophor® BA.

In accordance with the present invention, there are provided methods for prevention and treatment of oomycete infections which occur in aquatic organisms including fish and fish eggs, and methods of disinfecting equipment used for raising aquatic organisms, wherein the equipment is contaminated with an oomycete.

The methods of the invention comprise a step of contacting either the aquatic organism, or the equipment used for raising the aquatic organism, with an effective amount of at least one stilbene derivative, particularly a 4,4'-bis-(1,3,5-triazinylamino)stilbene-2,2'-disulfonic acid derivative of Formula (I):

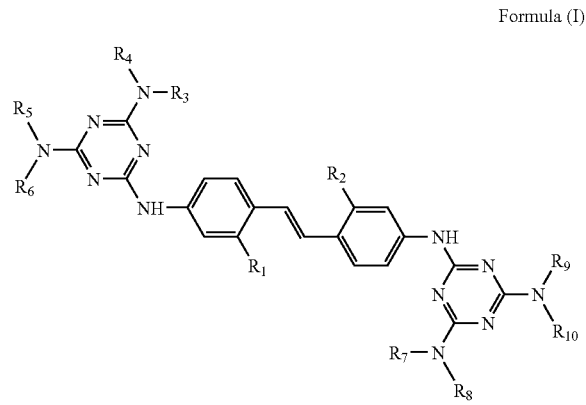

Formula (I)

In Formula I, $R_1$ and $R_2$ are the same or different and are each independently selected from the group consisting of $SO_3H$, $SO_3Na$, $SO_3K$, $SO_3NH_4$ and H. Further in Formula I, $R_3$ to $R_{10}$ are the same or different, and $R_3$ to $R_{10}$ are selected from the group consisting of H; linear or branched $C_1$-$C_6$ alkyl; linear or branched $C_2$-$C_6$ alkenyl, wherein said alkyl or alkenyl are each independently unsubstituted or substituted with a hydroxyl, carboxyl, or carboxamide group; phenyl; and phenyl substituted with $R_1$ or $R_2$ wherein $R_1$ and $R_2$ are as defined above; or, one or more of $R_3$ and $R_4$, $R_5$ and $R_6$, $R_7$ and $R_8$ or $R_9$ and $R_{10}$, together with the nitrogen to which they are attached, form a heterocyclic ring which can further comprise one or more additional heteroatoms selected from N, O and S.

In particular embodiments of the methods of the invention, two or more of $R_3$, $R_4$, $R_7$ and $R_8$ are the same and are selected from the group consisting of $CH_2CH_2OH$, $CH_2CHOHCH_3$, $CH_2CH_2CONH_2$, $CH_3$ and H; or one or more of $R_3$ and $R_4$, $R_7$ and $R_8$ together with the nitrogen to which they are attached, form a morpholinyl ring.

In other embodiments, two or more of $R_5$, $R_6$, $R_9$ and $R_{10}$ are the same and are selected from the group consisting of phenyl and phenyl substituted with $SO_3Na$. In other embodiments, $R_1$ and $R_2$ are the same and are selected from $SO_3H$ and $SO_3Na$. In still other embodiments, $R_1$ and $R_2$ are different and are selected from $SO_3H$, $SO_3Na$, $SO_3K$, $SO_3NH_4$ and H.

Examples of 4,4'-bis-(1,3,5-triazinylamino)stilbene-2,2'-disulfonic acid derivatives useful in the invention include, but are not limited to 4,4'-bis-(6-anilino-1,4-bis)-2-hydroxyethyl)amino)-1,3,5-triazin-2-yl)amino)stilbene-2,2'-disulfonic acid; disodium 4,4'-bis-(6-anilino-1,4-bis)-2-hydroxyethyl)amino)-1,3,5-triazin-2-yl)amino)stilbene-2,2'-disulfonate; potassium sodium 4,4'-bis-(6-anilino-4-bis)-2-hydroxyethyl)amino)-1,3,5-triazin-2-yl)amino)stilbene-2,2'-disulfonate; 2,2'-stilbenedisulfonic acid,4,4'-bis-(4-anilino-6-((2-hydroxyethyl)methylamino)-s-triazin-2-yl)amino)-, disodium salt; disodium 4,4'-bis[(4-anilino-6-morpholino-1,3,5-triazin-2-yl)amino]stilbene-2,2'-disulfonate; tetrasodium 4,4'-bis[[4-[bis(2-hydroxyethyl)amino]-6-(4-sulfonatoanilino)-1,3,5-triazin-2-yl]amino]stilbene-2,2'-disulfonate; tetrasodium 4,4'-bis[[4-[bis(2-hydroxypropyl)amino]-6-[(4-sulfonatophenyl)amino]-1,3,5-triazin-2-yl]amino]-stilbene-2,2'-disulfonate; and 2,2'-stilbenedisulfonic acid,4,4'-bis-[[4-[(2-carbamoylethyl)(2-hydroxylethyl)amino]-6-(p-sulfoanilino)-s-triazin-2-yl]amino]-, tetrasodium salt.

When the above-described compounds include one or more chiral centers, the stereochemistry of such chiral centers can independently be in the R or S configuration, or a mixture of the two. The chiral centers can be further designated as R or S or R,S or d,D, l,L or d,l, D,L.

DEFINITIONS

The term "$C_1$ to $C_6$ alkyl" as used herein refers to saturated radicals such as methyl, ethyl, n-propyl, isopropyl, n-butyl, iso-butyl, sec-butyl, tert-butyl, amyl, tert-amyl, hexyl and the like. Preferred $C_1$ to $C_6$ alkyl groups are methyl, ethyl and propyl. The $C_1$ to $C_6$ alkyl groups are optionally independently substituted with a hydroxyl, carboxyl or carboxamide group. Preferred substituents are hydroxyl and carboxamide groups. Exemplary substituted $C_1$ to $C_6$ alkyl groups are hydroxyethyl, hydroxypropyl and ethylcarboxamido. In specific embodiments of the 4,4'-bis-(1,3,5-triazinylamino)stilbene-2,2'-disulfonic acid derivatives of the invention, each of $R_5$, $R_6$, $R_7$ and $R_8$ are hydroxyethyl. In other specific embodiments, two of $R_5$ or $R_6$, and $R_7$ or $R_8$ are hydroxyethyl and two are H. In yet other embodiments, each of $R_5$, $R_6$, $R_7$ and $R_8$ are hydroxypropyl. In yet other embodiments, two of $R_5$ or $R_6$, and $R_7$ or $R_5$ are ethylcarboxamido and two are hydroxyethyl.

The term "$C_2$ to $C_6$ alkenyl" as used herein refers to unsaturated radicals such as vinyl, allyl, 2-butenyl, 3-butenyl, 2-pentenyl, 3-pentenyl, 4-pentenyl, 2-hexenyl, 3-hexenyl, 4-hexenyl, 5-hexenyl radicals attached at any appropriate carbon position and the like, as well as dienes and trienes of straight and branched chains. The $C_1$ to $C_6$ alkenyl groups are optionally substituted with hydroxyl, carboxyl, or carboxamide groups.

The 4,4'-bis-(1,3,5-triazinylamino)stilbene-2,2'-disulfonic acid derivatives can be optionally substituted at any one or more of $R_3$ to $R_{10}$ with phenyl groups or with phenyl groups substituted with $R_1$ or $R_2$, wherein $R_1$ and $R_2$ are as defined above. In specific embodiments, two of $R_3$ or $R_4$, and $R_9$ or $R_{10}$ are phenyl and two are H.

The term "phenyl substituted with $R_1$ or $R_2$" as used herein refers to a phenyl group substituted with one or more moieties chosen from the group consisting of $SO_3H$, $SO_3Na$, $SO_3K$, $SO_3NH_4$ and H. In specific embodiments, two of $R_3$ or $R_4$, and $R_9$ or $R_{10}$ are phenyl substituted with $SO_3Na$ and two are H.

The term "heterocyclic ring which can further comprise one or more heteroatoms selected from N, O and S" as used herein refers to optionally substituted five-membered to eight-membered rings that can have 1 to 4 heteroatoms, such as nitrogen, oxygen and/or sulfur, in particular oxygen, in conjunction with a nitrogen ring atom. These five-membered to eight-membered rings may be saturated, fully unsaturated, partially unsaturated or aromatic, with fully saturated rings being preferred. The heterocyclic rings according to the invention include, but are not limited to, morpholino, piperidinyl, piperazinyl, imidazolyl, 2-amino-imidazoyl, pyrrolo, heptylmethyleneimino, thiazole, triazole, tetrazole pyrrolidine, pyrazole, imidazole, pyridine, thiomorpholine, oxazole and pyrimidine.

The term "effective amount" as used herein refers to an amount of at least one 4,4'-bis-(1,3,5-triazinylamino)stilbene-2,2'-disulfonic acid derivative of the invention which is effective to treat, prevent, protect, repair, detoxify or disinfect an aquatic organism against an oomycete infection or to treat, prevent, protect, repair, detoxify or disinfect equipment against oomycete contamination, upon contact with the at least one 4,4'-bis-(1,3,5-triazinylamino)stilbene-2,2'-disulfonic acid derivative over some period of time.

4,4'-bis-(1,3,5-triazinylamino)stilbene-2,2'-disulfonic acid derivatives

The 4,4'-bis-(1,3,5-triazinylamino)stilbene-2,2'-disulfonic acid derivatives useful for the methods of the present invention include known whitening agents which have been used in the textile, detergent and paper industries. Such compounds are commonly known as C.I. Fluorescent Brighteners (having various numerical suffixes), and include, for example, C.I. Fluorescent Brightener 28, C.I. Fluorescent Brightener 113, C.I. Fluorescent Brightener 28/113, C.I. Fluorescent Brightener 220, C.I. Fluorescent Brightener 235, C.I. Fluorescent Brightener 260 and C.I. Fluorescent Brightener 263. C.I. Fluorescent Brighteners possess a common backbone molecular structure, and differ with respect to the substituents attached to either or both of the benzene and triazine rings, and with respect to the nature of the salt or acid derivative. Further, C.I. Fluorescent Brighteners are sold under various trade names and one compound may have a number of different synonyms. For example, disodium 4,4'-bis-(6-anilino-1,4-bis)-2-hydroxyethyl)amino)-1,3,5-triazin-2-yl)amino) stilbene-2,2'-disulfonate is known by the common name C.I. Fluorescent Brightener 28 and has been sold under the trade names Calcofluor® White, Cellufluor® and Phorwite®, among others. C.I. Fluorescent Brighteners are supplied as aqueous solution or powder formulations. For example, Blankophore® BA Liquid (Lanxess) is an aqueous solution comprising the mixed salt potassium sodium 4,4'-bis-(6- anilino-4-bis)-2-hydroxyethyl)amino)-1,3,5-triazin-2-yl) amino)stilbene-2,2'-disulfonate.

Other 4,4'-bis-(1,3,5-triazinylamino)stilbene-2,2'-disulfonic acid derivatives are also envisioned, and can be created by changing the substituents attached to either or both of the benzene and triazine rings, and/or the salt derivative. They may be in the form of salts, mixed salts, free acids and mixtures thereof. Such derivatives can be readily designed and synthesized by those of skill in the art.

The 4,4'-bis-(1,3,5-triazinylamino)stilbene-2,2'-disulfonic acid derivatives useful for the methods of the present invention may be provided in various formulations, for example, aqueous solutions, or powder formulations which are reconstituted with water. Aqueous formulations may contain agents which aid in solubility. Powder formulations may contain dispersing agents or dedusting agents. Such excipients should be appreciably soluble in water and be non-toxic to living organisms and the environment.

The 4,4'-bis-(1,3,5-triazinylamino)stilbene-2,2'-disulfonic acid derivatives useful for the methods of the present invention are appreciably soluble in water. The water solubility can in general, be increased by increasing the numbers of hydrophilic substituents such as sulfonate and hydroxyl groups, as is known to those skilled in the art.

The 4,4'-bis-(1,3,5-triazinylamino)stilbene-2,2'-disulfonic acid derivatives useful for the methods of the present invention are stable to hydrolysis, but may be subject to photodegradation in the hydrosphere, due to having UV absorption maxima between 340 to 360 nm in water. They may or may not be readily biodegradable; in the latter case, they are preferably adsorbed onto sludge in wastewater treatment systems.

The 4,4'-bis-(1,3,5-triazinylamino)stilbene-2,2'-disulfonic acid derivatives useful for the methods of the present invention have minimal impact on living creatures and on the environment. For example, the overall relative safety of C.I. Fluorescent Brighteners 28, 220, 235, 260 and 263 has been documented. These compounds are reported to have low toxicity to fish, annelids and bacteria and low to moderate toxicity to aquatic invertebrates and algae. With respect to mammals, they have low acute or repeated dose oral toxicity, are not mutagenic or clastogenic, are not reproductive or developmental toxicants, and are generally not irritating or sensitizing to skin and eyes (*Stilbene Fluorescent Whitening Agents Category*, submitted to the US Environmental Protection Agency by the ETAD Fluorescent Whitening Agent Task Force, Oct. 6, 2005).

Putative Mechanism of Action

Without wishing to be bound to any particular theory or mechanism of action, the therapeutic and prophylactic efficacy of the 4,4'-bis-(1,3,5-triazinylamino)stilbene-2,2'-disulfonic acid derivatives of the invention against oomycetes may be attributed to the ability of such compounds to disrupt oomycete cell walls. Various 4,4'-bis-(1,3,5-triazinylamino) stilbene-2,2'-disulfonic acid derivatives are known to bind to polysaccharides having β-glucosidic linkages, such as occur in cellulose (a β-(1,4) linked polymer of D-glucose units). Oomycete cell walls in general, contain cellulose and other β-glucan polymers, for example β-(1,2) linked and (β-(1,6) linked polymers of D-glucose units, as the major structural elements. While the proportions and linkages of these polymers vary among different oomycete genera and species, these macromolecules are the likely targets of the 4,4'-bis-(1, 3,5-triazinylamino)stilbene-2,2'-disulfonic acid derivatives of the invention. Intercalation of such compounds with fully formed and/or nascent β-glucosidic polymers compromises the integrity of the cell wall, ultimately leading to cell lysis.

The mechanism of action may be similar or analogous to that exerted by 4,4'-bis-(1,3,5-triazinylamino)stilbene-2,2'-disulfonic acid derivatives against true fungi, in which chitin (a β-(1,4) linked polymer of N-acetyl-D-glucosamine units) is the major structural component of cell walls.

Oomycete Pathogens and Diseases of Aquatic Organisms

The methods of the invention are effective against disease causing oomycetes which attack aquatic organisms, including fish and shellfish. Oomycetes include but are not limited to *Achyla* spp., *Aphanomyces* spp., *Branchiomyces* spp., *Brevilegnia* spp., *Dermocystidium* spp., *Dictyuchus* spp., *Ichthyophonus* spp., *Isoachyla* spp., *Leptolegnia* spp., *Leptomitus* spp., *Protoachyla* spp., *Pythium* spp., *Saprolegnia* spp., and *Thraustotheca* spp.

Organisms of the genus *Saprolegnia*, and especially *S. parasitica*, are responsible for saprolegniosis, one of the most common and significant oomycete infections occurring in fish. In common with all saprophytic oomycetes, *Saprolegnia* spp. feeds by secreting degradative enzymes onto the surface to which it is attached, thus enabling absorption of nutrients such as proteins and carbohydrates. Saprolegniosis often occurs as a secondary infection following damage to the fish integument (skin and gills) caused by parasites, viruses, bacterial infections and abrasion. Other predisposing factors include overcrowding, intensive handling and water pollution. Less commonly, *Saprolegnia* spp. can act as a primary pathogen infecting fish which have not incurred integument damage. Such attacks are temperature-dependant, usually occurring at low temperatures, possibly as a consequence of a reduced immune response. As well as being a threat to fish, *Saprolegnia* spp. also infects fish eggs.

Saprolegniosis appears as grey/white patches on the skin or gills that resemble tufts of cotton wool. At a later stage they may become brown or green as they trap sediment or algae. If the fish is removed from the water, the fungus appears as a slimy matted mass. *Saprolegnia* spp. normally establishes as small, focal infections that then spread rapidly over the body or gills. As it spreads, healthy tissue is destroyed. There is often little inflammation unless there is an underlying bacterial infection. Microscopic examination shows broad, non-septate hyphae, typical of oomyetes.

*Achyla* spp. cause a disease similar to saprolegniosis, and under similar conditions.

Branchiomycosis or "gill rot" is caused by *Branchiomyces sanguinis* and *B. demigrans*. Both species are found in fish suffering from environmental stress, such as low pH, low dissolved oxygen, high algal bloom or high ammonia levels. Affected fish appear lethargic and the gills are striated or marbled with the pale areas representing infected and dying tissue.

Oomycete infections are transmitted among fish by infectious zoospores which are released from infected tissues.

Aquatic Organisms

According to the invention, the method of preventing or treating an oomycete infection can be applied to a wide variety of aquatic organisms that are infected with or at risk of infection by oomycete pathogens. Aquatic organisms include but are not limited to fish and eggs thereof. The fish include economically useful fish raised in commercial fish farming settings, cultured fish, aquarium fish and decorative fish of all ages which live in fresh water and sea water. The fish include but are not limited to barramundi, bass, bream, carp, catfish, chub, eel, elver, flounder, gilthead, guppy, halibut, koi, labrax, mullet, paddlefish, plaice, pompano, redfish, red-drum, salmon, sole, sturgeon, tilapia, trout, tuna and whitefish. Aquatic organisms further include but are not limited to shellfish, both molluscs and crustaceans, for example abalone, clam, crab, geoduck, mussel, lobster, oyster, prawn, shrimp and urchin.

Equipment Used for Raising Aquatic Organisms

According to the invention, the method of disinfecting equipment used for raising aquatic organisms is directed to equipment that is used for containing, raising, manipulating and treating the aquatic organisms, for example fish. Detection of oomycete disease in the aquatic organisms is a sufficient indicator that the equipment is contaminated, either by direct contact with the infected aquatic organisms harboring hyphal mycelia or by contact with the dispersed zoospores. Such equipment requires disinfection, so as to eliminate the possibility of recurrent infection, for example, in mature fish that have had an oomycete disease and have been treated according to the invention, or new infection in juvenile fish or eggs introduced to or exposed to the equipment. The equipment includes aquariums, basins, baths, cages, filters, meshes, nets, ponds, pools, tanks, transfer apparatus, troughs, thermometers and the like.

Parasitic Infections

Parasitic infections are often concurrent with or accompany oomycete infections, for example in commercial fish farming settings and in hobby aquariums. Fish subjected to stress and/or adverse environmental conditions may be vulnerable to such concurrent infections due to immune system suppression. Parasitic infections include those caused by *Amyloodinium* spp., *Argulus* spp., *Ascocotyle* spp., *Bothricephalus* spp., *Camallanus* spp., *Capilaria* spp., *Centrocestus* spp., *Chilodonella* spp., *Coccidia* spp., *Contracaecum* spp., *Cryptobia* spp., *Cryptocaryon* spp., *Dactylogyrus* spp., *Dermocystidium* spp., *Ergasilus* spp., *Euclinostomum* spp., *Gyrodactylus* spp., *Hexamita* spp., *Ichtyobodo* spp., *Ichtyophtirius* spp., *Lernaea* spp., *Metacercarius* spp., *Microsporidia* spp., *Myxosporea* spp., *Oodinium* spp., *Sanguinicola* spp., *Sessiline* spp., *Spironucleus* spp., *Tetrahymena* spp., *Trichodina* spp., *Trichodinella* spp. and *Tripartiella* spp.

The inventors of the present invention have surprisingly found that treatment with at least one 4,4'-bis-(1,3,5-triazinylamino)stilbene-2,2'-disulfonic acid derivative according to the invention is effective for treating at least one parasitic infection which is concurrent with an oomycete infection in fish.

Applications of the Invention

The method of preventing or treating an oomycete infection described herein can be applied in a variety of situations, including: (1) prophylactic prevention of seasonal disease outbreaks in commercial fish farming settings; (2) intervention and therapeutic treatment of infected fish; (3) treatment prior to anticipated stress conditions, for example changes in water quality including temperature decrease; (4) pretreatment and treatment after transferring and/or shipping fish; (5) treatment of "sick" fish for home hobbyists; and (6) maintenance of health in fish for small and large scale, domestic and commercial growth and for scientific experiments. The method of the invention is effective for application at both an early stage of infection, when no clinical signs may be apparent, as well as at later stages of infection when the oomycete infection is established and causes a high rate of mortality.

For preventing or treating an oomycete infection, aquatic organisms are contacted with an effective amount of at least one 4,4'-bis-(1,3,5-triazinylamino)stilbene-2,2'-disulfonic acid derivative. The contacting step may be carried out by transferring aquatic organisms, for example fish or shellfish in a commercial setting, from their original containment facility, for example a pond or tank, to a fresh containment facility containing an effective amount of at least one 4,4'-bis(1,3,5-triazinylamino)stilbene-2,2'-disulfonic acid derivative. This method is preferable when oomycete infection has been detected, for example, on the bodies of fish, requiring appropriate intervention and therapeutic treatment. For such therapeutic treatment, the density of fish in the fresh containment facility may be maintained at the same ratio as that in the original containment facility, or may be preferably decreased to ease stress conditions.

Alternately, the organisms may be maintained in their original containment facility, to which is added an effective amount of at least one 4,4'-bis-(1,3,5-triazinylamino)stilbene-2,2'-disulfonic acid derivative. This method may be preferred for economic reasons when the method of the invention is applied for prevention of oomycete infection, either as a routine procedure or in anticipation of expected stress conditions.

In the methods described herein for preventing or treating an oomycete infection and for disinfecting equipment, the contacting step is carried out with at least one 4,4'-bis-(1,3,5-triazinylamino)stilbene-2,2'-disulfonic acid derivative which may be provided in a variety of forms. A solution is generally preferred, but other forms are also envisioned, for example, dissolving tablets, gels, and impregnated materials which release the active material upon exposure to water, or which are suitable for direct application to contaminated equipment.

When a solution is used, a concentration in the range of about 20 to about 200 mg/liter of water may be suitable for most applications. The lowest concentration which achieves preventative, therapeutic, or disinfecting efficacy against oomycete infection or contamination is preferable, in order to minimize costs and the amount of compounds released into waste water systems. The preferred concentration may further depend on duration of the treatment and on the age and condition of the treated aquatic organisms. For example, contacting of tilapia fish with 25 mg/liter of Blankophor® BA for 8 hours has been found to be effective for preventing and treating saprolegniosis in tilapia fish.

An effective amount of the at least one 4,4'-bis-(1,3,5-triazinylamino)stilbene-2,2'-disulfonic acid derivative is that which achieves preventative (prophylactic), therapeutic, or disinfecting efficacy, as appropriate. The effective amount may be determined in pilot experiments. An effective amount for preventing oomycete infection refers to the amount or concentration brought into contact with an aquatic organism such that the aquatic organism is prevented from becoming infected in the presence of an oomycete pathogen to which the aquatic organism is susceptible. For example, a prophylactic treatment is deemed to be effective in a situation where the mortality rate due to oomycete pathogen challenge in fish pretreated with a 4,4'-bis-(1,3,5-triazinylamino)stilbene-2,2'-disulfonic acid derivative prior to challenge is reduced by a significant percentage, for example, 25 to 100%, of the rate observed in fish not pretreated. An effective amount for treating an oomycete infection refers to the amount or concentration brought into contact with an aquatic organism infected with an oomycete pathogen such that the aquatic organism is protected against the development or progression of an infection, disease, or mortality associated with the oomycete pathogen. For example, a therapeutic treatment is deemed to be effective in a situation where the mortality rate in fish first challenged with an oomycete pathogen and subsequently treated with a 4,4'-bis-(1,3,5-triazinylamino)stilbene-2,2'-disulfonic acid derivative is reduced by a significant percentage, for example, 25 to 100%, of the rate observed in infected, non-treated fish. An effective amount for disinfecting equipment contaminated with an oomycete refers to the amount or concentration brought into contact with the equipment such that the equipment no longer harbors oomycete mycelia or zoospores. For example, a disinfecting treatment is deemed to be effective in a situation where the disinfected equipment is monitored for the presence of oomycete mycelia and/or zoospores after the disinfecting treatment and found to be reduced by a significant percentage, for example, 25 to 100%, of that observed before the disinfecting treatment.

Contacting of aquatic organisms and/or contaminated equipment with at least one 4,4'-bis-(1,3,5-triazinylamino) stilbene-2,2'-disulfonic acid derivative may be carried out over a period of about 2 hours to about 16 hours. For example, a period of about eight hours has been found to be effective in infected fish. If time is a limitation, relatively shorter periods may be used, optionally with higher concentrations of at least one 4,4'-bis-(1,3,5-triazinylamino)stilbene-2,2'-disulfonic acid derivative. If time is not a limiting factor, longer periods may be used and may be preferable for disinfecting equipment. Further, the contacting periods may be repeated at regular intervals, for example, 48 hours after completion of the first contacting period, to ensure complete eradication of the oomycete infection or contamination.

The foregoing description of the specific embodiments will so fully reveal the general nature of the invention that others can, by applying current knowledge, readily modify and/or adapt for various applications such specific embodiments without undue experimentation and without departing from the brand concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Susceptibility Testing of *Saprolegnia parasitica*

The in vitro susceptibility of *Saprolegnia parasitica* T-1 and *S. parasitica* CBS 540.67 to various compounds was determined by the agar-dilution and broth macrodilution methods.

Material and Methods

*Saprolegnia parasitica* Isolates

*Saprolegnia parasitica* T-1 isolate was obtained from skin lesions on moribund tilapia exhibiting signs of saprolegniosis. For the purpose of isolation, a small part of the skin and scales covered with hyphae was dried, and cut with a sterile scalpel blade, then placed onto Glucose-Peptone-Penicillin-Streptomycin (GP-PS) plates containing 3 g/l glucose, 1 g/l peptone, trace micronutrients and 250 mg/l each Penicillin-G and Streptomycin Sulphate, and incubated at 18° C.

After incubation for 3-4 days, a block of agar from the edge of the fungal colony was cut off and placed in sterile Petri plates, containing double distilled water and sterile Clover seeds, in order to obtain new bacteria-free colonies. The molecular identification was done by Dr. Alexandra Riethmueller (University of Kassel, Germany) by sequencing of the ITS regions of the 18S rDNA.

The isolates were kept at 18° C. on GP-PS plates, and were transferred every month.

*S. parasitica* CBS 540.67 is a publicly available strain.

Reagents

Compounds tested for activity against *S. parasitica* are summarized in Table 1.

Susceptibility Testing

Two methods were used, each suitable for a different phase of the asexual life cycle of *Saprolegnia* spp.: i) the broth macrodilution method, for determination of susceptibility of zoospores and cysts; and ii) the agar-dilution method for determination of susceptibility of filamentous hyphae. Each compound was tested three times in each method. Malachite Green was used as positive control.

Broth Macrodilution Method

This method is a modification of the method used for molds according to EUCAST 7.1 (European Committee on Antibiotic Susceptibility Testing) and CLSI/NCCLS M27-A2 (Clinical Laboratory Standards Institute/National Committee for Clinical Laboratory Standards). For inoculum preparation, *S. parasitica* isolates were cultured on GP-PS for 7 days with sterile clover seeds at 18° C. Clover seeds (~20) covered with mycelium were removed and added to 40 ml of RPMI-1640 broth medium (Sigma; prepared according to NCCLS instructions) and incubated at 18° C. for 4-7 days. Cysts and zoospores free from hyphae were collected, and an inoculum of ~$10^3$ CFU/ml as measured by hemacytometer counting, was prepared in RPMI. Stock solutions of the tested compounds were prepared in water or in DMSO, as indicated in Table 2. Fluorescent Brightener 28 stock solution was prepared by adding 40% KOH gradually to a 10 mg/ml solution in water, until it was clear, then it was filtered twice through a 0.2 μm cellulose acetate nonpyrogenic sterile filter (Schleicher & Schuell, Dassel, Germany).

Twofold serial dilutions of the resulting stock solutions were set in RPMI-1640 medium in a volume of 0.1 ml. Final drug concentrations in the test tubes ranged from $1\times10^4$ to 0.01 mg/L. Inoculum of 0.9 ml was added to each of a sterile tube containing 0.1 ml of the serially diluted drug. Two tubes containing drug-free medium and two tubes containing drug-free inoculum were used as controls. The inoculated tubes were incubated at room temperature (15-20° C.) for 24 h. The growth in each tube was then evaluated visually. The MIC-0 was defined as the lowest drug concentration that resulted in complete inhibition of visible growth.

Agar-Dilution Method

This method is a modification of the method presented by Bailey (Bailey, T. A. (1983) Prog. Fish Cult. 45:24-27), and was used for the susceptibility testing of *Saprolegnia* hyphae. Twofold serial dilutions were prepared in double distillated sterile water with final drug concentrations ranging from 10,000 to 0.01 mg/L in a final volume of 1.0 ml. Melted (56° C.) RPMI-1640 agar medium (Sigma) was prepared according to NCCLS instructions, and then added to each tube containing drug or water control. The mixture was vortexed, and poured into small plates. After agar solidification a small measured piece, taken from a 7-10 day old culture of *S. parasitica* T-1 on GP-PS medium was placed upside down on each plate. The plates were incubated at room temperature (15-20° C.) for 24 h. The growth in each plate was then estimated visually, and the MIC values were defined as the minimal concentration that resulted in complete inhibition of visible growth compared to a drug-lacking control.

TABLE 1

Compounds tested against S. parasitica

| Compound | Source |
| --- | --- |
| Malachite Green | Reactif R.A.L, Paris, France |
| Copper sulfate | Sigma, St. Louis, Mo., USA |
| Formaldehyde | Sigma, St. Louis, Mo., USA |
| Fluorescent Brightener 28 | Sigma, St. Louis, Mo., USA |
| Pyceze ® (bronopol) | Novartis, Essex, UK |
| Blankophore ® BA | Lanxess, Leverkusen, Germany |
| Hydrogen peroxide | Ecolab, Zohar Dalia, Israel |
| Sodium percarbonate | Ecolab, Zohar Dalia, Israel |
| Clinador ® (Enilconazole) | Dorvet, Nes Ziona, Israel |
| Amphotericin B | Dumex, Copenhagen, Denmark |
| Fungizone ® (amphotericin deoxycholate) | Squibb, Middlessex, UK |
| Amphotericin B-arabinogalactan conjugate (AmB-AG) | Falk, R., Domb, A. J. & Polacheck, I. (1999) Antimicrobial Agents and Chemotherapy 43, 1975-81 |
| C-TAB | BDH Chemicals, Poole, UK |
| Triton X-100 | BDH Chemicals, Poole, UK |
| Tween ®-20 | BDH Chemicals, Poole, UK |
| Tween ®-80 | BDH Chemicals, Poole, UK |
| Sodium dodecylsulfate (SDS) | BDH Chemicals, Poole, UK |
| Digitonin | Merck, Dermstadt, Germany |
| Carcid ® | Carmel Resins, Atlit, Israel |
| Carcil ® C-50 | Carmel Resins, Atlit, Israel |
| Septocil ® | Carmel Resins, Atlit, Israel |
| Agrosept ® | Ketox, Copenhagen, Denmark |
| Neem oil | Tomer-teva, Israel |
| Saprofin ® | Dropco Laboratorios, Chile |
| NaCl | Sigma, St. Louis, Mo., USA |

Results

The two methods for determining in vitro susceptibility of S. parasitica were highly reproducible (98 and 95% respectively). The MIC values obtained using the two S. parasitica isolates were similar for each compound tested, and the difference between them was statistically insignificant. The MIC values of the tested compounds are presented in Table 2, with each result representing the geometric mean of three independent tests. The lowest MIC values were consistently obtained with Malachite Green (0.06 mg/L). Other compounds that exhibited high in vitro activity (MIC≦10 mg/L) against S. parasitica were as follows: Fluorescent Brightener 28, all the tested cationic detergents, Digitonin (a non-ionic detergent), sodium percarbonate and hydrogen peroxide. The lowest activity was detected with natural oils, Tween-20 and sodium chloride (MIC≧200 mg/L). Despite the high in vitro activity observed with Fluorescent Brightener 28 (MIC values of 1 and 5 mg/L in both methods), it was eliminated from subsequent studies on in vivo activity, toxicity and therapeutic efficacy, due to its extremely high cost.

TABLE 2

MIC values (mg/L) of various compounds

| | | S. parasitica T-1 | | S. parasitica CBS 540.67 | |
| --- | --- | --- | --- | --- | --- |
| Compound | Solvent | Macrodilution | Agar-dilution | Macrodilution | Agar-dilution |
| Antimicrobials | | | | | |
| Malachite Green | DDW | 0.06 | 0.06 | 0.06 | 0.06 |
| Sodium percarbonate | DDW | 5 | NA* | 2.5 | NA |
| Hydrogen peroxide | DDW | 10 | NA | 8 | NA |
| Copper sulfate | DDW | 40 | 80 | 80 | 120 |
| Formaldehyde | DDW | 100 | 100 | 100 | 100 |
| Pyceze ® (bronopol) | DDW | 100 | 100 | 100 | 200 |
| Sodium chloride | DDW | 30,000 | NA | 30,000 | NA |
| Antifungal agents | | | | | |
| Fungizone ® | DDW | 0.25 | 5 | 0.5 | 5 |
| Amphotericin B | DMSO | 0.5 | 5 | 0.25 | 2.5 |
| AmB-AG conjugate | DDW | 0.5 | 5 | 0.25 | 5 |
| Enilconazole | DDW | 1 | 5 | 1 | 5 |
| Fluorescent Brighteners | | | | | |
| Fluorescent Brightener 28 | DDW | 1 | 5 | 2 | 5 |
| Blankophore ® BA | DDW | 100 | 200 | 200 | 200 |
| Detergents & disinfectants | | | | | |
| Carcid ® (cationic) | DMSO | 5 | 50 | 5 | 100 |
| Carcil ® C-50 (cationic) | DMSO | 5 | 50 | 5 | 50 |
| Septocil ® (cationic) | DMSO | 5 | 50 | 5 | 100 |
| CTAB (cationic) | DMSO | 5 | 10 | 5 | 50 |
| Agrosept ® (cationic) | DMSO | 10 | 50 | 5 | 50 |
| Digitonin (non ionic) | DMSO | 2.5 | 10 | 2.5 | 20 |
| Triton X-100 (non ionic) | DMSO | 50 | 200 | 100 | 200 |
| Tween ® 20 (non ionic) | DMSO | 500 | 1,000 | 250 | 1,000 |
| Tween ® 80 (non ionic) | DMSO | 100 | 200 | 100 | 200 |
| SDS (anionic) | DMSO | 100 | 500 | 250 | 500 |
| Natural oils | | | | | |

TABLE 2-continued

MIC values (mg/L) of various compounds

| Compound | Solvent | S. parasitica T-1 Macrodilution | Agar-dilution | S. parasitica CBS 540.67 Macrodilution | Agar-dilution |
| --- | --- | --- | --- | --- | --- |
| Saprofin ® | DMSO | 400 | 400 | 400 | 400 |
| Neem oil | DMSO | >1,000 | >1,000 | >1,000 | >1,000 |

NA = Non-applicable

Example 2

Toxicity Testing in Tilapia

Compounds evaluated in Example 1 were further evaluated for their toxic effects in tilapia fish.

Material and Methods $LC_{50}$ values were determined by static short-term tests as a measure of the relative acute lethal toxicity for tilapia (*Standard methods for the evaluation of water and wastewater* (1985) 16th ed. American Public Health Association, Washington, D.C. p. 689-819).

Hybrid tilapia (*Oreochromis niloticus* X *Oreochromis aureus*) having an average weight of 20 g, were kept in 100 liter polyethylene tanks at a density of 1 fish per 10 liters, at a constant temperature of 21° C. for three weeks before the initiation of the experiment by addition of a test compound to each tank. The toxicities of hydrogen peroxide, sodium percabonate and Blankophore® BA were also evaluated at temperatures of 18° C. and 15° C. For the latter experiments, fish were acclimated to the required temperature for three weeks prior to addition of the test compound to the tank. Fish were treated with 5 different concentrations of each test compound, determined according to the MIC values of each compound.

Mortality of fish was recorded up to 96 h. Water parameters ($O_2$, $NH_4^+$, $NO_2^-$, pH and $Cl^-$) were monitored throughout the experiment and were maintained within acceptable limits. The presented results are the mean of two separate experiments.

All procedures for care and treatment of fish were in accordance with the *Guide for the Care and Use of Laboratory Animals* (Hebrew University of Jerusalem, Israel) and were approved by the Committee for Ethical Conduct in the Care and Use of Laboratory Animals.

Results $LC_{50}$ values determined for various compounds are presented in FIG. 1. Compounds having an $LC_{50}$ value 5 to 10 times higher than that of their respective MIC were selected for further study for therapeutic efficacy in the tilapia-saprolegniosis model.

The $LC_{50}$ values of copper sulfate, Pyceze®, and all the tested disinfectants, detergents and antifungal agents were lower, similar or insignificantly different from their respective MIC values and were accordingly excluded from the therapeutic efficacy study. Significantly higher differences were demonstrated for Malachite Green, formaldehyde, hydrogen peroxide, sodium percarbonate, and Blankophore® BA i.e. the ratio between the $LC_{50}$ value and the MIC value was >20. Some of the compounds with low toxicity at 18° C. were also tested at a lower temperature (15° C.). The results are presented in Table 3 and clearly indicate that the toxicity of hydrogen peroxide, and to a greater extent, sodium percarbonate, increased significantly at 15° C. In contrast, the $LC_{50}$ value of Blankophor® BA remained high, even at the lower temperature, indicating its relative lack of toxicity for the fish.

TABLE 3

Toxicity of compounds ($LC_{50}$) in tilapia at various temperatures

| Compound | $LC_{50}$ (mg/L) 15° C. | 18° C. | 25° C. |
| --- | --- | --- | --- |
| Hydrogen peroxide | 75 | ≧100 | >100 |
| Sodium percarbonate | 27 | >100 | >100 |
| Blankophor ® BA | >2,000 | >2,000 | >2,000 |

Example 3

Toxicity Testing of Blankophor® BA in Various Fish Species

Materials and Methods $LC_{50}$ values for Blankophor® BA in various fish species were determined as in Example 2, except that fish were acclimated to 21° C. for three weeks, and then to 15° C. for another two weeks before the initiation of the experiment. Following acclimation to 15° C., Blankophor® BA (100, 200, 500, 1,000 or 2,000 mg/L) was added to the tanks, and mortality of fish was recorded up to 96 h. Water parameters ($O_2$, $NH_4^+$, $NO_2^-$, pH and $Cl^-$) were monitored throughout the experiment and were maintained within acceptable limits. The presented results are the mean of two separate experiments. The fish used were: hybrid tilapia (*Oreochromis niloticus* X *O. aureus*), average weight 20 g; grey mullet (*Mugil cephalus*), average weight 70 g; common carp (*Cyprinus carpio*), average weight 25 g; hybrid striped bass (*Morone saxatilis* X *M. chrysops*), average weight 25 g, and grass carp (*Ctenopharyngodon idella*), average weight 25 g.

Results

The $LC_{50}$ values observed for the fish species tested were all greater than 2000 mg/L. These results are consistent with the results presented in Example 2 and support the conclusion that compounds of the invention, such as Blankophor® BA, are substantially non-toxic to a variety of fish species, including those of commercial importance.

Example 4

Therapeutic Efficacy of Blankophor® BA in an Early Infection Model of Saprolegniosis Material and Methods Hybrid tilapia (*Oreochromis niloticus* X *Oreochromis aureus*), with an average weight of 20 g were treated against ectoparasites using 25 μg/ml of formaldehyde (37% v/v) two weeks prior to the experiment, and were maintained at a constant temperature of 21° C. in a 100 liter polyethylene tank. The water tank was cooled from an initial temperature of 21° C. to 14° C. over a period of 10 days. The water was kept at a constant temperature of 14° C. and the fish were acclimated for 4 days. Physical stress of abrasion was then applied by agitating 40 fish for 10 seconds within a plastic net (30×20 cm). Following this, a sterile stainless steel tea infuser containing 60 clover-seeds covered with hyphae of *Saprolegnia parasitica* T-1 (7 day old culture on GP-PS medium at 18° C.) was added to each tank, in which the fish density was 20 fish per 100 liters. This treatment lasted 48 h and allowed the dispersion of zoospores that were produced. The density of the zoospores in the water was determined according to the method described below, and was estimated as $5\times10^2$-$2\times10^3$ zoospores per liter. The fish were then transferred to different tanks, and treated with Blankophor® BA (200, 100, 50 or 25 mg/L) or Malachite Green (0.25 mg/L) for 8 h at 13-14° C., with 10 fish per 100 L water. The treatments were applied on $2^{nd}$, $4^{th}$ and $6^{th}$ day following initiation of the experiment. The fish were monitored for 14 days for the presence of any lesion covered with hyphae, indicative of *Saprolegnia* infection. Skin biopsies of diseased and moribund fish were checked microscopically (10× and 40× magnification). Morbidity and mortality was monitored daily. Moribund and or dead fish were removed from all tanks during the experimental period.

The determination of zoospore density in the water was performed according to Willoughby, L. G. (1994) *Fungi and fish diseases*, Pisces Press, Stirling, Scotland p. 57.

In brief, a 1 liter sample of water from the 100 liter tank was divided into 1 and 10 ml aliquots in sterile Petri dishes. Each sample was diluted with water to give a final volume of 20 ml and then one sterile clover seed was added in order to attract and keep the zoospores. All the water samples were incubated at room temperature for 72 h allowing spore germination. The density of the zoospores was determined according to the number of seeds covered with visible mycelium.

Results

Figure 2:
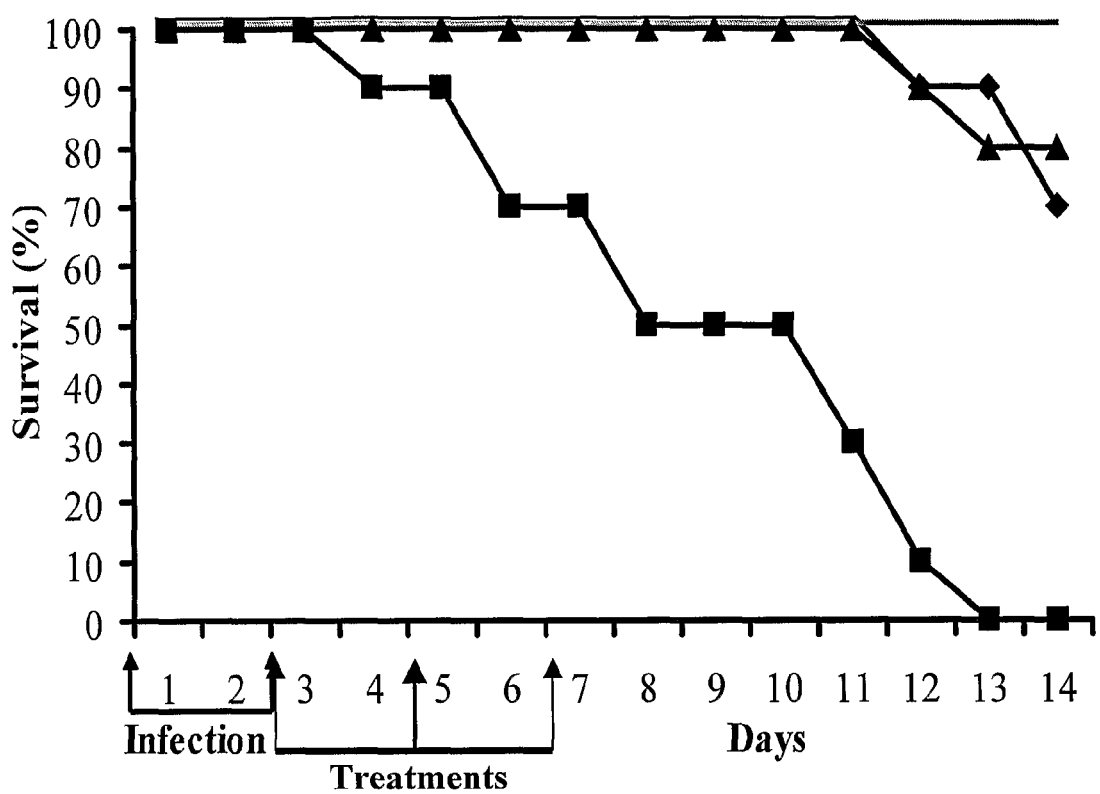
FIG. 2 illustrates the therapeutic efficacy of Blankophor® BA (comprising potassium sodium 4,4'-bis-(6-anilino-4-bis)-2-hydroxyethyl)amino)-1,3,5-triazin-2-yl)amino)stilbene-2,2'-disulfonate) and Malachite Green (4-[(4-dimethylaminophenyl)phenyl-methyl]-N,N-dimethyl-aniline) in a tilapia-saprolegniosis early infection model system. Tilapia fish were treated with Blankophor® BA 100 mg/L (♦) or 200 mg/L (●), or with Malachite Green 0.25 mg/L (▲) on the $2^{nd}$, $4^{th}$ and $6^{th}$ day after exposure to *Saprolegnia*. Control, (■).

*Saprolegnia*-infected fish were treated with Blankophor® BA at different concentrations (100 and 200 mg/L), in accordance with the determined MIC values. Treatments were carried out on the $2^{nd}$, $4^{th}$ and $6^{th}$ days after the initiation of the infection, and each treatment was for a period of 8 h. Fish treated with 0.25 mg/L Malachite Green served as a positive treatment control. Fish were monitored for 14 days. All dead fish were clinically evaluated, and exhibited significant *Saprolegnia* lesions, as determined microscopically and confirmed by positive culture of *Saprolegnia*. The results of the treatment with Blankophor® BA are summarized in FIG. 2, and show that Blankophor® BA is as effective as Malachite Green in enabling survival of fish following *Saprolegnia* infection. All fish treated with Blankophor BA survived for at least 10 days following initiation of the infection, in contrast to untreated fish which progressively died from the $3^{rd}$ day.

Due to the high efficacy of the treatment with 100 mg/L Blankophor® BA, additional experiments were performed using lower concentrations of Blankophor® BA (50 and 25 mg/L). As in the previous experiments, infected fish were treated in tanks containing different concentrations of the compound on the $2^{nd}$, $4^{th}$ and $6^{th}$ days after the initiation of the infection. In addition, two additional treatment regimens were added i.e. 50 mg/L (administered on the $2^{nd}$ and $9^{th}$ days after initiation of the infection) and 100 mg/L (administered on the $2^{nd}$ day after initiation of the infection). The results are summarized in FIG. 3 and indicate that Blankophor® BA was highly effective in preventing and treating early stage saprolegniosis infection in tilapia, even at a concentration as low as 25 mg/L.

Clinical observation of fish treated with high dosages (50 and 100 mg/L) of Blankophor® BA indicated that the specimens were free of lesions (a typical clinical sign) and furthermore, were negative upon culture for *Saprolegnia*. In addition, biopsies of scale and fin material indicated significant differences in the *Saprolegnia* hyphae removed from fish treated with Blankophor® BA 25 (mg/L) versus that removed from non-treated fish. Specifically, the former exhibited "normal" *Saprolegnia* hyphal structure, while the latter exhibited hyphae which were severely damaged, and considerably slimmer.

Figure 3:
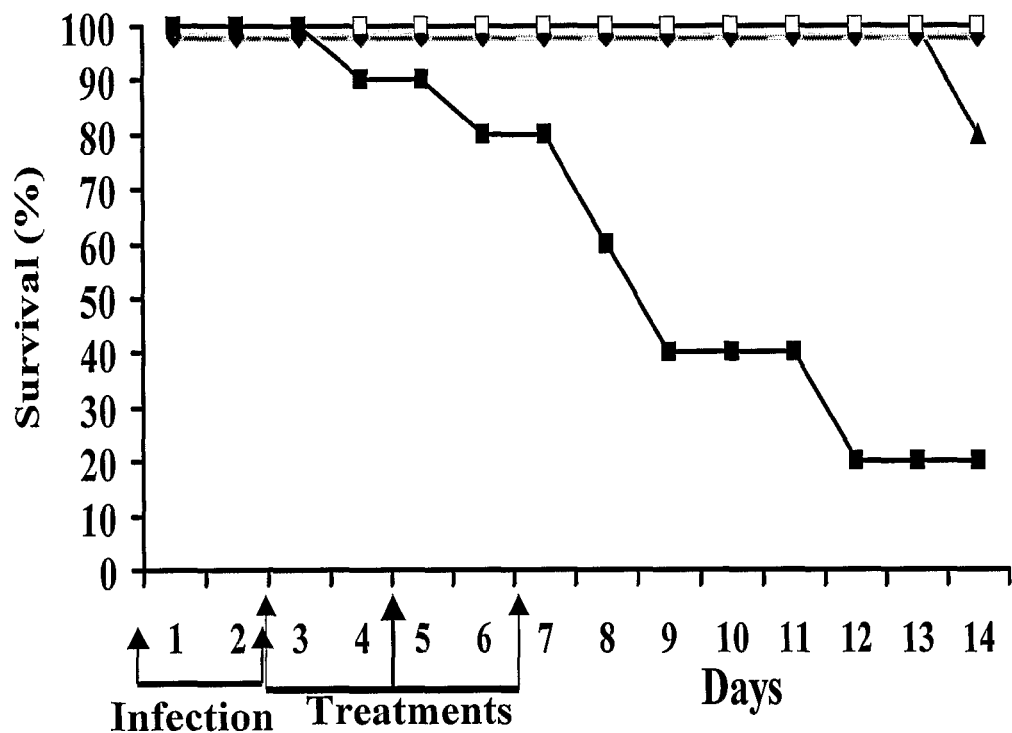
FIG. 3 illustrates the therapeutic efficacy of Blankophor® BA, formaldehyde and Malachite Green in a tilapia-saprolegniosis early infection model system. Tilapia fish were treated with Blankophor® BA 25 mg/L (▲) or 50 mg/L (♦), Malachite Green 0.25 mg/L (□) or formaldehyde 50 mg/L (●) on the $2^{nd}$, $4^{th}$ and $6^{th}$ day after exposure to *Saprolegnia*. In additional experiments, tilapia fish were treated with Blankophor® BA 50 mg/L on the $2^{nd}$ and $9^{th}$ day after exposure (Δ), or 100 mg/L on the $2^{nd}$ day after exposure (◇). Control, (■).

Formalin (37% formaldehyde v/v) was also tested in the tilapia-saprolegniosis model. At a concentration of 100 mg/L (administered on the 2nd, 4th and $6^{th}$ days after the initiation of the infection) 70% of the fish died within 14 days (data not shown). At a concentration of 50 mg/L, the therapeutic efficacy was observed to be similar to that of Blankophor® BA (FIG. 3). Formalin is not a feasible treatment for saprolegniosis however, since formaldehyde has a number of serious deleterious effects on animals and the environment. For example, it is a neurotoxin and probable carcinogen for humans; it decreases the soluble oxygen concentration in water, and is an algaecide.

Example 5

Therapeutic Efficacy of Blankophor® BA in an Established Infection Model of Saprolegniosis Materials and Methods Tilapia were exposed to *S. parasitica* and treated with Blankophor® BA (100, 50 and 25 mg/L), as described in Example 4, with the exception that Blankophor® BA treatment was started on the $3^{rd}$ day after initiation of the infection, and repeated on the $8^{th}$ day. By the starting point of the Blankophor® BA treatment, approximately 50% of the fish had established infection, as indicated by the presence of white skin lesions and a mortality rate of approximately 30%.

Results

Figure 4:
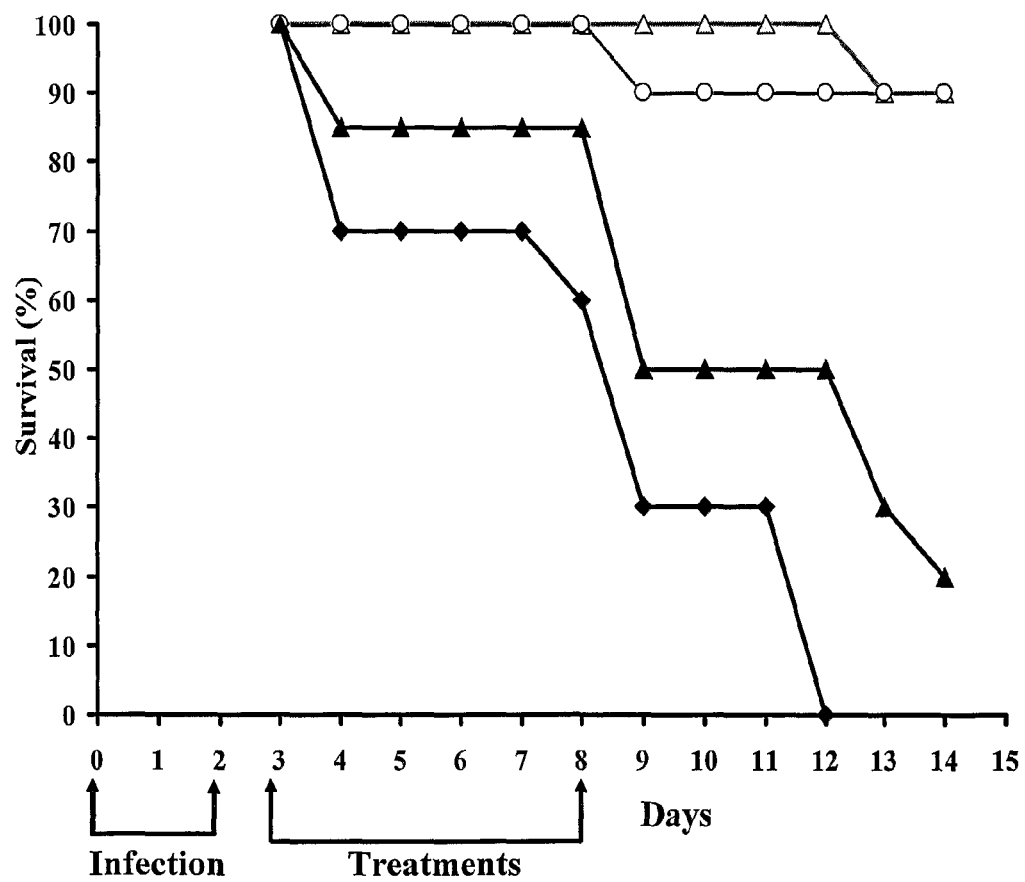
FIG. 4 illustrates the therapeutic efficacy of Blankophor® BA, in a tilapia-saprolegniosis established infection model system. Tilapia fish were treated with Blankophor® BA 100 mg/L (Δ), 50 mg/L (○) or 25 mg/L (▲) on the $3^{rd}$ and $8^{th}$ day after exposure to *Saprolegnia*. Control, (♦).

FIG. 4 shows that in this model of established saprolegniosis, treatment with Blankophor® BA (50 and 100 mg/L) was highly effective in promoting survival of infected fish. The difference between the non-treated control and Blankophor-treated fishes was highly significant ($p<0.01$).

Example 6

Non-Randomized Field-Trial of Blankophor® BA Treatment for Concurrent Oomycete and Parasitic Diseases Following transfer of 2000 hybrid tilapia fish (20-30 g) to a cement pond ($1\times10^5$ L, 21 to 25° C.), white patches of filamentous mycelium were observed on the body and fins of fish, covering in most cases about 80% of the body surface. The mycelia appeared about four days after the transfer, presumably due to opportunistic infection by *Saprolegnia* sp. following handling stress. Death of 20 to 30 fish per day was recorded. All the dead fish were covered with mycelium, characteristic of *Saprolegnia* sp., and were also found to be infected with the parasites *Gyrodactilus* sp. and *Trichodina* sp.

The water capacity in the pond was decreased to $3\times10^4$ L, and treatment with Blankophor® BA (50 mg/L) was initiated. A regimen of 3 treatments (8 h each) with 48 hours intervals between them was used.

Significant reduction in the prevalence and intensity of saprolegniosis was observed after the first treatment; no further deaths were recorded and the fish returned to their normal behavior. The fish were visually and microscopically examined 2 days after the end of the treatments, and were found to be free of both *Saprolegnia* sp. and the parasites *Gyrodactilus* sp. and *Trichodina* sp.

Example 7

Scanning Electron Microscopy Analysis of the Effect of Blankophor® BA on *S. parasitica*

Materials and Methods

*S. parasitica* T-1 hyphae and cysts from a 5 day RPMI-1640 broth culture, were exposed to different concentrations of Blankophor® BA (10, 25, 100 or 1,000 mg/L) for different periods of time. The specimens were fixed overnight in 2% glutaraldehyde, then with 1% $OSO_4$ for 2 h at room temperature, and dehydrated in ascending concentrations of alcohol (25-100%) and dried. The samples were viewed with a Leo 982 optical scanning electron microscope at an acceleration of 6 kV.

Results

Figure 5A:
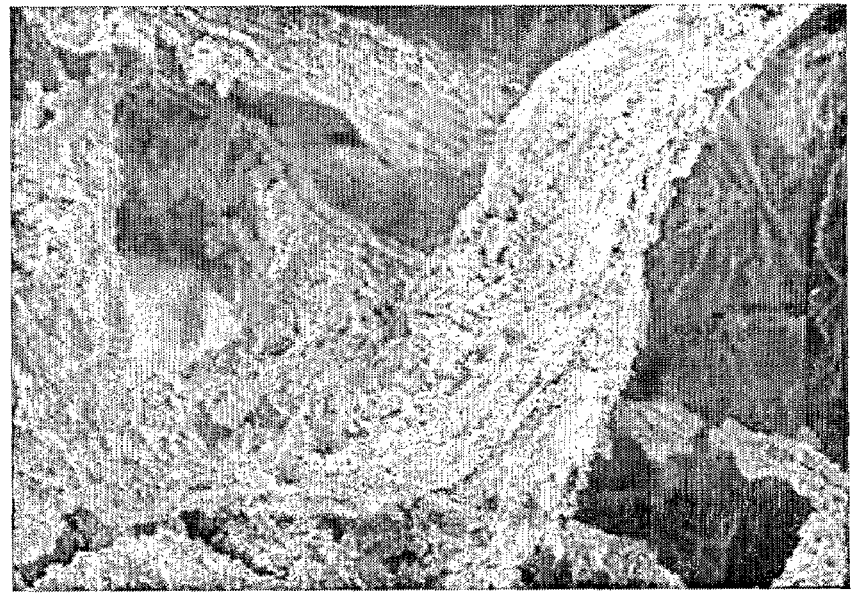
FIG. 5 shows scanning electron microscopy of cell walls of *Saprolegnia* treated with (panel A) and without (panel B) Blankophor® BA. Magnification: 3000×.
Figure 5B:
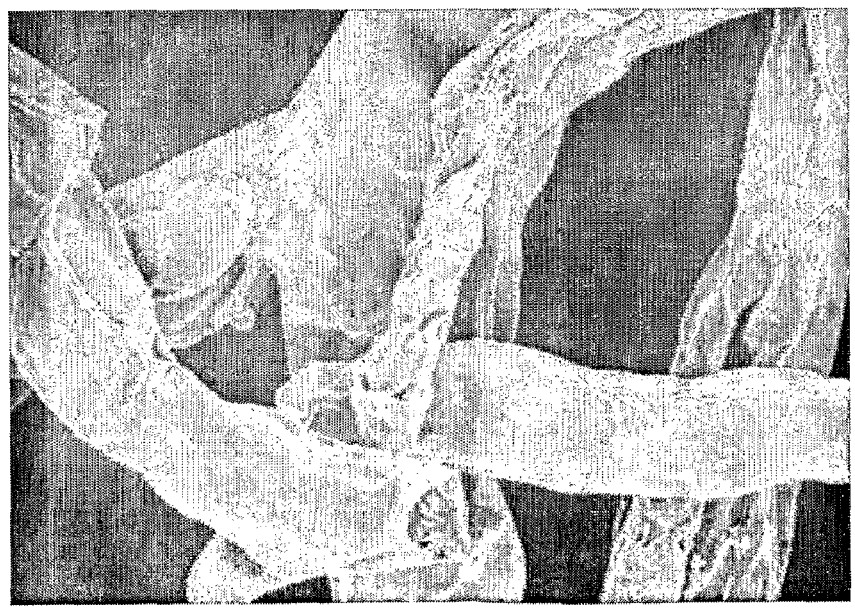

Scanning Electron Microscopy (SEM) of *S. parasitica* hyphae and cysts shows that treatment with Blankophor® BA (1,000 mg/L) results in highly distorted, wrinkled, and collapsed cell walls (FIG. 5A), whereas the untreated control displays undamaged cell walls (FIG. 5B). These results strongly support the conclusion that Blankophor® BA disrupts the integrity of the cell wall in *Saprolegnia*. Accordingly, the mechanism of action of Blankophor® BA may involve one or more specific targets in the oomycete cell wall.

Examples 8-10 describe a battery of biological toxicity studies, carried out to verify that compounds of the invention are non-toxic to non-target organisms.

Example 8

Toxicity of Blankophor® BA to Mice

Materials and Methods

Blankophor® BA was prepared at various concentrations in 5% dextrose and filter sterilized by passage through a sterile 0.2 µm pore size cellulose acetate filter (Schleicher & Schuell, Dassel, Germany). Male albino ICR mice (weight 30 g) were injected through the tail vein with various doses of Blankophor® BA. Each dosage form was administered intravenously as single bolus injection of 0.1 ml of the same dose every 10 min to a group of 10 mice until death was observed. The survival of mice that received the maximal tolerated dose (MTD) was monitored for 8 days.

Results

The maximal tolerated dose (MTD) of Blankophor® BA in ICR mice was found to be >1 g/kg, confirming that it is a safe compound, as previously determined (*Stilbene Fluorescent Whitening Agents Category*, submitted to the US Environmental Protection Agency by the ETAD Fluorescent Whitening Agent Task Force, Oct. 6, 2005).

Example 9

Toxicity of Blankophor® BA to Zooplankton

*Daphnia* sp. is a small (0.2 to 5 mm in length) planktonic crustacean, commonly used as a model for aquatic toxicity.

Materials and Methods

*Daphnia* (~1,000 cells/L water) was exposed to Blankophor® BA 100 and 1,000 mg/L). The experiment was carried out in covered flasks (100 ml/per flask), equipped with air supply. The flasks were incubated at room temperature for 48 h, and the *Daphnia* motility was recorded.

Results

After 48 h of incubation, no difference was noted between *Daphnia* that was exposed to Blankophor® BA, and the non-exposed control group, indicating that Blankophor® BA is not toxic to this organism.

Example 10

Toxicity of Blankophor® BA to Phytoplankton

The Delayed Fluorescent Excitation Spectroscopy (DFES) method was used for qualitative and quantitative assessment of the influence of Blankophor® BA on the natural population of phytoplankton, and on specific algae strains. Delayed fluorescence is a unique characteristic of photosynthetically active cells, as it is an outcome of recombination that takes place in the thylakoids in the dark (Yacobi Y. Z., V. Gerhardt, Y. Gonen-Zurgil, and A. Sukenik. 1998. Delayed fluorescence excitation spectroscopy: a rapid method for the qualitative and quantitative assessment of natural population of phytoplankton. Wat. Res. 00:1-6).

Materials and Methods:

Samples from Lake Kinneret and pure cultures of *Peridinium* sp. and *Microcystis* sp. were exposed to Blankophor® BA (100 mg/L), for a few minutes and the concentration of chlorophyll-a was determined (in duplicate) according to the excitation spectrum examined (range from 400 to 730 nm). In addition, the exposed and non-exposed samples were assessed for carbon uptake with a $^{14}C$ technique.

Results

Figure 6:
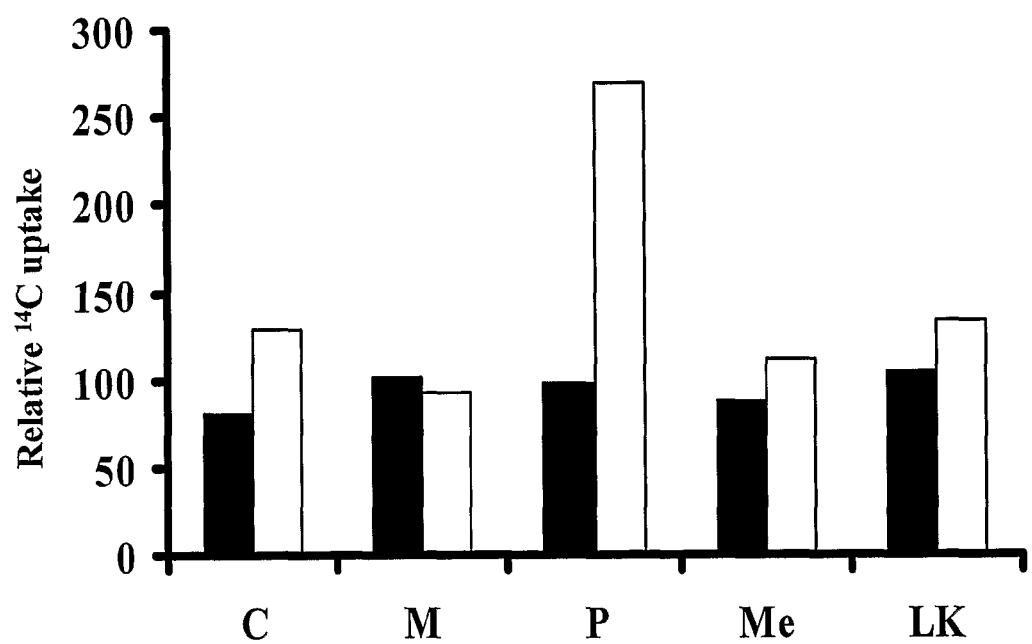
FIG. 6 illustrates the effect of exposure to Blankophor® BA (100 mg/L) (□) on photosynthetic activity in pure cultures of *Chlorella* (C), *Microcystis* (M), *Peridinium* (P) and *Melosira* (Me), and in samples from Lake Kinneret (LK), as determined by $^{14}C$-uptake. Control, (■).

Photosynthetic activity in Lake Kinneret water samples was not deleteriously affected following exposure to Blankophor® BA (100 mg/L), since the total chlorophyll concentration was 9.2 µg/L (average), as compared to 4.6 µg/L (average) prior to exposure. Similarly, when a pure culture of *Microcystis* was exposed to Blankophor® BA (100 mg/L), no difference in photosynthetic activity was noted as compared to non-treated samples The results of the $^{14}C$-carbon uptake study, shown in FIG. 6, are consistent with the DFES experiments, and indicate that exposure to Blankophor® BA did not decrease the photosynthetic activity in pure cultures of various algal species (*Chlorella, Microcystis, Peridinium* and *Melosira*), nor in the total algae population in Lake Kinneret. Taken together, these preliminary findings support the conclusion that Blankophor® BA is not toxic to phytoplankton.

CONCLUSIONS

In order to identify an effective treatment for saprolegniosis to replace hazardous prior art treatments, such as Malachite Green, a number of antimicrobial and antifungal agents, detergents and disinfectants were evaluated (Table 4). Based on the combination of results obtained in the various assay systems, and parameters of animal safety, environmental impact and cost, each of the compounds was assigned a utility index (UI). Of the compounds fully evaluated, Blankophor® BA has the highest UI. This strongly suggests that 4,4'-bis-(1,3,5-triazinylamino)stilbene-2,2'-disulfonic acid derivatives, as provided by Blankophor® BA, can serve as therapeutically effective, safe and economical alternatives to Malachite Green.

TABLE 4

Utility of various compounds against *Saprolegnia*

| Compound | Activity in vitro (MIC) | Toxicity[1] | Therapeutic efficacy | Cost | Utility Index[2] (UI) |
|---|---|---|---|---|---|
| Hydrogen peroxide | High (10 mg/L) | Moderate | ND | Low | Moderate (problematic in earth pond) |
| Sodium chloride | Extremely Low (30,000 mg/L) | ND | ND | High | Low |
| Sodium percarbonate | High (10 mg/L) | High (in low temperature) | ND | Low | Low |
| Detergents, including Agrosept | Variable | High | Non effective | Low | Low |
| Formaldehyde | Moderate (100 mg/L) | Moderate | Effective | Low | Low (negative safety and environmental profile) |
| Pyceze ® | Moderate (100 mg/L) | Moderate | Non effective | High | Low |
| Amphotericin B | High (0.1-0.5 mg/L) | Moderate | ND | High | Low |
| Blankophor ® BA | Moderate (100 mg/L) | Low | Very Effective | Low | High |

[1]Toxicity was defined as: high = 50 ppm; moderate = 50-200 ppm; and low = >1000 ppm.
[2]Utility Index (UI): Index measuring the usefulness of the compound by considering the parameters of toxicity, therapeutic efficacy and cost.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A method of preventing or treating an oomycete infection in an aquatic organism, the method comprising the step of contacting the aquatic organism with an effective amount of at least one 4,4'-bis-(1,3,5-triazinylamino)stilbene-2,2'-disulfonic acid derivative of Formula (I):

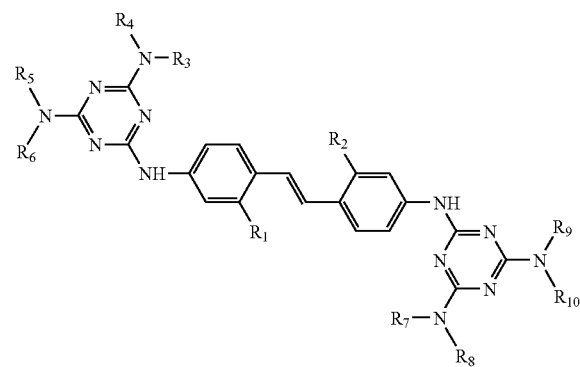

Formula (I)

wherein $R_1$ and $R_2$ are the same or different and are each independently selected from the group consisting of $SO_3H$, $SO_3Na$, $SO_3K$, $SO_3NH_4$ and H;

$R_3$ to $R_{10}$ are the same or different and are selected from the group consisting of H; linear or branched $C_1$-$C_6$ alkyl; linear or branched $C_2$-$C_6$ alkenyl, wherein said alkyl or alkenyl are each independently unsubstituted or substituted with a hydroxyl, carboxyl, or carboxamide group; phenyl; and phenyl substituted with $R_1$ or $R_2$ wherein $R_1$ and $R_2$ are as defined above;

or one or more of $R_3$ and $R_4$, $R_5$ and $R_6$, $R_7$ and $R_8$ or $R_9$ and $R_{10}$, together with the nitrogen to which they are attached, form a heterocyclic ring which can further comprise one or more additional heteroatoms selected from N, O and S; and salts, hydrates, solvates and polymorphs thereof; thereby preventing or treating the oomycete infection in said aquatic organism.

2. The method of claim 1, wherein two or more of $R_3$, $R_4$, $R_7$ and $R_8$ are the same and are selected from the group consisting of $CH_2CH_2OH$, $CH_2CHOHCH_3$, $CH_2CH_2CONH_2$, $CH_3$ and H; or one or more of $R_3$ and $R_4$, $R_7$ and $R_8$ together with the nitrogen to which they are attached, form a morpholinyl ring.

3. The method of claim 1, wherein two or more of $R_5$, $R_6$, $R_9$ and $R_{10}$ are the same and are selected from the group consisting of phenyl and phenyl substituted with $SO_3Na$.

4. The method of claim 1, wherein $R_1$ and $R_2$ are the same and are selected from the group consisting of $SO_3H$ and $SO_3Na$, or wherein $R_1$ and $R_2$ are different and are selected from the group consisting of $SO_3H$, $SO_3Na$, $SO_3K$, $SO_3NH_4$ and H.

5. The method of claim 1, wherein the 4,4'-bis-(1,3,5-triazinylamino)stilbene-2,2'-disulfonic acid derivative is selected from the group consisting of 4,4'-bis-(6-anilino-1,4-bis)-2-hydroxyethyl)amino)-1,3,5-triazin-2-yl)amino)stilbene-2,2'-disulfonic acid; disodium 4,4'-bis-(6-anilino-1,4-bis)-2-hydroxyethyl)amino)-1,3,5-triazin-2-yl)amino) stilbene-2,2'-disulfonate; potassium sodium 4,4'-bis-(6-anilino-4-bis)-2-hydroxyethyl)amino)-1,3,5-triazin-2-yl) amino)stilbene-2,2'-disulfonate; 2,2'-stilbenedisulfonic acid, 4,4'-bis-(4-anilino-6-((2-hydroxyethyl)methylamino)-s- triazin-2-yl)amino)-, disodium salt; disodium 4,4'-bis[(4-anilino-6-morpholino-1,3,5-triazin-2-yl)amino]stilbene-2,2'-disulfonate; tetrasodium 4,4'-bis[[4-[bis(2-hydroxyethyl)amino]-6-(4-sulfonatoanilino)-1,3,5-triazin-2-yl]amino]stilbene-2,2'-disulfonate; tetrasodium 4,4'-bis[[4-[bis(2-hydroxypropyl)amino]-6-[(4-sulfonatophenyl)amino]-1,3,5-triazin-2-yl]amino]-stilbene-2,2'-disulfonate; and 2,2'-stilbenedisulfonic acid,4,4'-bis-[[4-[(2-carbamoylethyl)(2-hydroxyethyl)amino]-6-(p-sulfoanilino)-s-triazin-2-yl]amino]-,tetrasodium salt.

6. The method of claim 1, wherein the oomycete is selected from the group consisting of *Saprolegnia* spp., *Aphanomyces* spp, and *Branchiomyces* spp.

7. The method of claim 6, wherein the oomycete is *Saprolegnia parasitica*.

8. The method of claim 1, wherein the aquatic organism is selected from the group consisting of fish, fish eggs and shellfish.

9. The method of claim 8 wherein the fish is selected from the group consisting of barramundi, bass, bream, carp, catfish, chub, eel, elver, flounder, gilthead, guppy, halibut, koi, labrax, mullet, paddlefish, plaice, pompano, redfish, reddrum, salmon, sole, sturgeon, tilapia, trout, tuna and whitefish.

10. The method of claim 1, wherein the at least one 4,4'-bis-(1,3,5-triazinylamino)stilbene-2,2'-disulfonic acid derivative is provided in a form selected from the group consisting of a solution, a dissolving tablet, a gel and an impregnated material.

11. The method of claim 10, wherein the at least one 4,4'-bis-(1,3,5-triazinylamino)stilbene-2,2'-disulfonic acid derivative is provided in the form of a solution at a concentration of about 20 to about 200 mg/L.

12. The method of claim 11, wherein the at least one 4,4'-bis-(1,3,5-triazinylamino)stilbene-2,2'-disulfonic acid derivatives is present in the solution at a concentration of about 25 mg/L.

13. The method of claim 1, wherein the contacting step is for a period of about 2 to about 16 hours, or for a period of about 8 hours.

14. The method of claim 13, wherein the contacting step is repeated at 48 hour intervals.

15. The method of claim 1, wherein the oomycete infection is concurrent with or accompanied by a parasitic infection, wherein the parasitic infection is caused by at least one parasite selected from the group consisting of *Amyloodinium* spp., *Argulus* spp., *Ascocotyle* spp., *Bothricephalus* spp., *Camallanus* spp., *Capilaria* spp., *Centrocestus* spp., *Chilodonella* spp., *Coccidia* spp., *Contracaecum* spp., *Cryptobia* spp., *Cryptocaryon* spp., *Dactylogyrus* spp., *Dermocystidium* spp., *Ergasilus* spp., *Euclinostomum* spp., *Gyrodactylus* spp., *Hexamita* spp., *Ichtyobodo* spp., *Ichtyophtirius* spp., *Lernaea* spp., *Metacercarius* spp., *Microsporidia* spp., *Myxosporea* spp., *Oodinium* spp., *Sanguinicola* spp., *Sessiline* spp., *Spironucleus* spp., *Tetrahymena* spp., *Trichodina* spp., *Trichodinella* spp, and *Tripartiella* spp.

16. A method of disinfecting equipment used for raising aquatic organisms, the method comprising the step of contacting the equipment with an effective amount of at least one 4,4'-bis-(1,3,5-triazinylamino)stilbene-2,2'-disulfonic acid derivative of Formula (I):

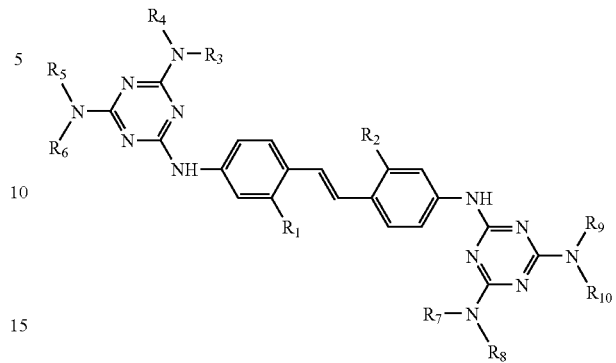

Formula (I)

wherein $R_1$ and $R_2$ are the same or different and are each independently selected from the group consisting of $SO_3H$, $SO_3Na$, $SO_3K$, $SO_3NH_4$ and H; and wherein $R_3$ to $R_{10}$ are the same or different and are selected from the group consisting of H; linear or branched $C_1$-$C_6$ alkyl; linear or branched $C_2$-$C_6$ alkenyl, wherein said alkyl or alkenyl are each independently unsubstituted or substituted with a hydroxyl, carboxyl, or carboxamide group; phenyl; and phenyl substituted with $R_1$ or $R_2$ wherein $R_1$ and $R_2$ are as defined above; or one or more of $R_3$ and $R_4$, $R_5$ and $R_6$, $R_7$ and $R_8$ or $R_9$ and $R_{10}$, together with the nitrogen to which they are attached, form a heterocyclic ring which can further comprise one or more additional heteroatoms selected from N, O and S; and salts, hydrates, solvates and polymorphs thereof; thereby disinfecting said equipment.

17. The method of claim 16, wherein two or more of $R_3$, $R_4$, $R_7$ and $R_8$ are the same and are selected from the group consisting of $CH_2CH_2OH$, $CH_2CHOHCH_3$, $CH_2CH_2CONH_2$, $CH_3$ and H; or one or more of $R_3$ and $R_4$, $R_7$ and $R_8$ together with the nitrogen to which they are attached, form a morpholinyl ring.

18. The method of claim 16, wherein two or more of $R_5$, $R_6$, $R_9$ and $R_{10}$ are the same and are selected from the group consisting of phenyl and phenyl substituted with $SO_3Na$.

19. The method of claim 16, wherein $R_1$ and $R_2$ are the same and are selected from the group consisting of $SO_3H$ and $SO_3Na$, or wherein $R_1$ and $R_2$ are different and are selected from the group consisting of $SO_3H$, $SO_3Na$, $SO_3K$, $SO_3NH_4$ and H.

20. The method of claim 16, wherein the 4,4'-bis-(1,3,5-triazinylamino)stilbene-2,2'-disulfonic acid derivative is selected from the group consisting of 4,4'-bis-(6-anilino-1,4-bis)-2-hydroxyethyl)amino)-1,3,5-triazin-2-yl)amino)stilbene-2,2'-disulfonic acid; disodium 4,4'-bis-(6-anilino-1,4-bis)-2-hydroxyethyl)amino)-1,3,5-triazin-2-yl)amino)stilbene-2,2'-disulfonate; potassium sodium 4,4'-bis-(6-anilino-4-bis)-2-hydroxyethyl)amino)-1,3,5-triazin-2-yl)amino)stilbene-2,2'-disulfonate; 2,2'-stilbenedisulfonic acid, 4,4'-bis-(4-anilino-6-((2-hydroxyethyl)methylamino)-s-triazin-2-yl)amino)-, disodium salt; disodium 4,4'-bis[(4-anilino-6-morpholino-1,3,5-triazin-2-yl)amino]stilbene-2,2'-disulfonate; tetrasodium 4,4'-bis[[4-[bis(2-hydroxyethyl)amino]-6-(4-sulfonatoanilino)-1,3,5-triazin-2-yl]amino]stilbene-2,2'-disulfonate; tetrasodium 4,4'-bis[[4-[bis(2-hydroxypropyl)amino]-6-[(4-sulfonatophenyl)amino]-1,3,5-triazin-2-yl]amino]-stilbene-2,2'-disulfonate; and 2,2'-stilbenedisulfonic acid,4,4'-bis-[[4-[(2-carbamoylethyl)(2-hydroxyethyl)amino]-6-(p-sulfoanilino)-s-triazin-2-yl]amino]-,tetrasodium salt.

21. The method of claim 16, wherein the equipment is contaminated with at least one oomycete.

22. The method of claim 16, wherein the at least one 4,4'-bis-(1,3,5-triazinylamino)stilbene-2,2'-disulfonic acid derivative is provided in a form selected from the group consisting of a solution, a dissolving tablet, a gel and an impregnated material.

23. The method of claim 22, wherein the at least one 4,4'-bis-(1,3,5-triazinylamino)stilbene-2,2'-disulfonic acid derivative is provided in the form of a solution at a concentration of about 20 to about 200 mg/L.

24. The method of claim 23, wherein the at least one 4,4'-bis-(1,3,5-triazinylamino)stilbene-2,2'-disulfonic acid derivatives is present in the solution at a concentration of about 25 mg/L.

25. The method of claim 16, wherein the contacting step is for a period of about 2 to about 16 hours, or for a period of about 8 hours.

26. The method of claim 25, wherein the contacting is repeated at 48 hour intervals.

27. The method of claim 16, wherein the equipment is further contaminated with at least one parasite selected from the group consisting of *Amyloodinium* spp., *Argulus* spp., *Ascocotyle* spp., *Bothricephalus* spp., *Camallanus* spp., *Capilaria* spp., *Centrocestus* spp., *Chilodonella* spp., *Coccidia* spp., *Contracaecum* spp., *Cryptobia* spp., *Cryptocaryon* spp., *Dactylogyrus* spp., *Dermocystidium* spp., *Ergasilus* spp., *Euclinostomum* spp., *Gyrodactylus* spp., *Hexamita* spp., *Ichtyobodo* spp., *Ichtyophtirius* spp., *Lernaea* spp., *Metacercarius* spp., *Microsporidia* spp., *Myxosporea* spp., *Oodinium* spp., *Sanguinicola* spp., *Sessiline* spp., *Spironucleus* spp., *Tetrahymena* spp., *Trichodina* spp., *Trichodinella* spp, and *Tripartiella* spp.

28. The method of claim 16, wherein the at least one oomycete is selected from the group consisting of *Saprolegnia* spp., *Aphanomyces* spp, and *Branchiomyces* spp.

* * * * *